United States Patent [19]

Yoshino et al.

[11] Patent Number: 5,721,246
[45] Date of Patent: Feb. 24, 1998

[54] HETEROBICYCLIC SULFONAMIDE AND SULFONIC ESTER DERIVATIVES

[75] Inventors: Hiroshi Yoshino, Chiba; Takashi Owa, Ibaraki; Tatsuo Okauchi, Ibaraki; Kentaro Yoshimatsu, Ibaraki; Naoko Sugi, Ibaraki; Takeshi Nagasu, Ibaraki; Yoichi Ozawa, Ibaraki; Nozomu Koyanagi, Ibaraki; Kyosuke Kito, Ibaraki, all of Japan

[73] Assignee: Eisai Co., Ltd., Tokyo, Japan

[21] Appl. No.: 433,493

[22] PCT Filed: Sep. 8, 1994

[86] PCT No.: PCT/JP94/01487

§ 371 Date: May 10, 1995

§ 102(e) Date: May 10, 1995

[87] PCT Pub. No.: WO95/07276

PCT Pub. Date: Mar. 16, 1995

[30] Foreign Application Priority Data

Sep. 10, 1993 [JP] Japan .................. 5-248624
Aug. 31, 1994 [JP] Japan .................. 6-207568

[51] Int. Cl.$^6$ .............. A61K 31/415; C07D 471/02; C07D 209/02
[52] U.S. Cl. .............. 514/300; 546/121; 546/277.4; 548/469; 548/370.1; 548/315.7
[58] Field of Search .............. 514/303, 300, 514/415; 546/113, 118, 121, 277.4; 548/469, 315.7, 370.1

[56] References Cited

U.S. PATENT DOCUMENTS 5,587,383 12/1996 Takatani et al. .................. 514/300

OTHER PUBLICATIONS

S. Siddiqui, B. S. Siddiqui, and S. Begum, "Some New Derivatives of Harmaline Series of Bases" Z. Natur forsch 41B(12), 1583–6, 1986.

Paul G. Gassman et al., *J. Chem. Soc. D.*, vol. 22, pp. 1437–1438, 1971.

Masanobu Tani et al., *Heterocycles*, vol. 34, No. 12, pp. 2349–2363, 1992.

Yasuoki Murakami et al., *Tetrahedron Letters*, vol. 30, No. 16, pp. 2099–2100, 1989.

*Primary Examiner*—Joseph L. Schofer
*Assistant Examiner*—Wu C. Cheng
*Attorney, Agent, or Firm*—Birch, Stewart, Kolasch & Birch, LLP

[57] ABSTRACT

Novel heterobicyclic sulfonamide and sulfonic ester derivatives represented by the following general formula(I), which exhibit an antitumor activity and are lowly toxic, and processes for the preparation thereof.

A sulfonamide derivative and a sulfonic ester derivative represented by the general formula (I) or a pharmacologically acceptable salt thereof:

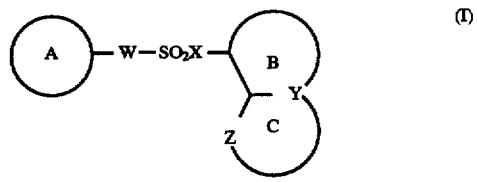

wherein A represents a monocyclic or bicyclic aromatic ring which may be substituted; B represents a six-membered unsaturated hydrocarbon ring or a six-membered unsaturated heterocycle containing one nitrogen atom, each of which may be substituted; C represents a five-membered heterocycle containing one or two nitrogen atoms which may be substituted; W represents a single bond or a group represented by formula —CH=CH—; X represents a group represented by formula —N($R^1$)— or oxygen; Y represents carbon or nitrogen; Z represents a group represented by formula —N($R^2$)— or nitrogen; and $R^1$ and $R^2$ may be the same or different from each other and each represent hydrogen or lower alkyl.

19 Claims, No Drawings

HETEROBICYCLIC SULFONAMIDE AND SULFONIC ESTER DERIVATIVES

The present invention relates to a novel sulfonamide or sulfonic ester derivative, a process for the preparation of the derivative, and a drug composition containing the same as an active ingredient.

1. Prior Art

Chemotherapeutic agents which have been used in the treatment of cancers include cyclophosphamide as an alkylating agent; methotrexate and fluorouracil as antimetabolites; adriamycin, mitomycin and bleomycin as antibiotics; vincristine and etoposide as drugs derived from plants; and cisplatin as a metal complex. However, these agents are insufficient in antitumor activity, so that the development of a new antitumor agent is eagerly expected.

Further, 2-sulfanylamidoquinoxaline derivatives (U.S. Pat. No. 4,931,433) and N-(2-anilino-3-pyridinyl) benzenesulfonamide derivatives (EP-A472053) have been reported as aromatic sulfonamide antitumor agents. No report has been made on aromatic sulfonic ester antitumor agents.

2. Disclosure of Invention

The present invention aims at providing a novel sulfonamide or sulfonic ester derivative which exhibits an excellent antitumor activity and is different from the antitumor agents of the prior art in basic skeleton. The present invention also aims at providing a process for the preparation of the derivative and a drug composition containing the same as an active ingredient.

In order to achieve the above aims, the inventors of the present invention have intensively studied to find an excellent antitumor agent. As a result of the studies, they have found that a novel heterobicyclic sulfonamide or sulfonic ester derivative exhibits an excellent antitumor activity and is lowly toxic. The present invention has been accomplished on the basis of this finding.

Namely, the present invention relates to a sulfonamide or sulfonic ester derivative represented by the general formula (I) or a pharmacologically acceptable salt thereof:

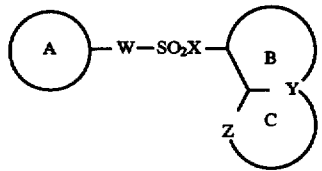

(I)

(wherein
A represents a monocyclic or bicyclic aromatic ring which may be substituted,
B represents a six-membered unsaturated hydrocarbon ring or a six-membered unsaturated heterocycle containing one nitrogen atom as the heteroatom, each of which may be substituted,
C represents a five-membered heterocycle containing one or two nitrogen atoms which may be substituted,
W represents a single bond or a group represented by formula —CH=CH—,
X represents a group represented by formula —N($R^1$)— or oxygen,
Y represents carbon or nitrogen,
Z represents a group represented by formula —N($R^2$)— or nitrogen, and
$R^1$ and $R^2$ may be the same or different from each other and each represent hydrogen or lower alkyl; with the proviso that (1) the case wherein A is 4-methylbenzene, W is a single bond, X is a group represented by formula —NH—, B is methoxybenzene and C is unsubstituted imidazole and (2) the case wherein A is 4-(acetamido) benzene or 4-aminobenzene, W is a single bond, X is a group represented by formula —NH—, B is unsubstituted benzene and C is unsubstituted pyrazole are excepted.)

Further, the present invention provides the use of the above compound as a drug.

Namely, the present invention also relates to a drug composition comprising a pharmacologically effective amount of a sulfonamide or sulfonic ester derivative or a pharmacologically acceptable salt thereof as set forth in claim 1, and a pharmacologically acceptable carrier; a method for the treatment of a tumor which comprises administering a sulfonamide or sulfonic ester derivative or a pharmacologically acceptable salt thereof as set forth in claim 1 to a patient in a pharmacologically effective dose; and the use of a sulfonamide or sulfonic ester derivative or a pharmacologically acceptable salt thereof as set forth in claim 1 in the preparation of an antitumor agent.

In the above general formula (I), A represents "a monocyclic or bicyclic aromatic ring which may be substituted", which refers to an aromatic hydrocarbon ring or an aromatic heterocycle containing at least one of nitrogen, oxygen and sulfur atoms, each of which may have one to three substituents thereon. Such aromatic ring defined with respect to A include pyrrole, pyrazole, imidazole, thiophene, furan, thiazole, oxazole, benzene, pyridine, pyrimidine, pyrazine, pyridazine, naphthalene, quinoline, isoquinoline, phthalazine, naphthyridine, quinoxaline, quinazoline, cinnoline, indole, isoindole, indolizine, indazole, benzofuran, benzothiophene, benzoxazole, benzimidazole, benzopyrazole and benzothiazole. They may have one to three substituents, and when two or three substituents are present, they may be either the same or different from each other. Examples of the substituents include amino which may be substituted with lower alkyl or lower cycloalkyl, lower alkyl, lower alkoxy, hydroxyl, nitro, mercapto, cyano, lower alkylthio, halogen, groups represented by formula —a—b [wherein a represents a single bond, —($CH_2$)$_k$—, —O—($CH_2$)$_k$—, —S—($CH_2$)$_k$— or —N($R^3$)—($CH_2$)$_k$— (wherein k is an integer of 1 to 5, and $R^3$ represents hydrogen or lower alkyl); and b represents a group represented by formula —$CH_2$—d (wherein d represents amino which may be substituted with lower alkyl, halogen, hydroxyl, lower alkylthio, cyano or lower alkoxy)], groups represented by formula —a—e—f [wherein a is as defined above; e represents —S(O)— or —S(O)$_2$—; and f represents amino which may be substituted with lower alkyl or lower alkoxy, lower alkyl, trifluoromethyl, —($CH_2$)$_m$—b or —N($R^4$)—($CH_2$)$_m$—b (wherein b is as defined above; $R^4$ represents hydrogen or lower alkyl; and m is an integer of 1 to 5)]; groups represented by formula —a—g—h [wherein a is as defined above; g represents —C(O)— or —C(S)—; and h represents amino which may be substituted with lower alkyl, hydroxyl, lower alkyl, lower alkoxy, —($CH_2$)$_n$—b or —N($R^5$)—($CH_2$)$_n$—b (wherein b is as defined above; $R^5$ represents hydrogen or lower alkyl; and n is an integer of 1 to 5)]; groups represented by formula —a—N($R^6$)—g—i [wherein a and g are each as defined above; $R^6$ represents hydrogen or lower alkyl; and i represents hydrogen or lower alkoxy or is as defined with respect to f]; groups represented by formula —a—N($R^7$)—e—f (wherein a, e and f are each as defined above; and $R^7$ represents hydrogen or lower alkyl); and groups represented by formula —($CH_2$)$_p$—j—($CH_2$)$_q$—b (wherein j represents oxygen or sulfur; b is as defined above; and p and q may be the same or different from each other and are each an integer of 1 to 5).

When the substituent is an amino group substituted with two alkyl groups, both of the alkyl groups may be combined to form a five- or six-membered ring. Further, when A is a nitrogenous heterocycle having a hydroxyl or mercapto group, this group may be present in the form of an oxo or thioxo group by resonance.

B represents "a six-membered unsaturated hydrocarbon ring or a six-membered unsaturated heterocycle containing one nitrogen atom as the heteroatom which may be substituted", which refers to benzene or pyridine which may be partially hydrogenated and may have one or two substituents on the ring, the substituents being either the same or different from each other when they have two substituents.

C represents "a five-membered heterocycle containing one or two nitrogen atoms which may be substituted", which refers to pyrrole, pyrazole or imidazole which may be partially hydrogenated and may have one or two substituents on the ring, the substituents being either the same or different from each other when they have two substituents.

Examples of the substituents for B and C include halogen, cyano, lower alkyl, lower alkoxy, hydroxyl, oxo, groups represented by formula —C(O)—r (wherein r represents hydrogen, amino which may be substituted with lower alkyl, lower alkyl, lower alkoxy or hydroxyl), amino substituted with lower alkyl, and trifluoromethyl.

The lower alkyl defined above with respect to $R^1$ and $R^2$ and the substituents for A, B and C in the general formula (I) is a linear or branched alkyl group having 1 to 6 carbon atoms, and examples of which include methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, among which methyl, ethyl, n-propyl, isopropyl, n-butyl and isobutyl are preferable, with methyl, ethyl, n-propyl and isopropyl being still preferable.

The lower cycloalkyl defined with respect to the substituent for A includes cyclopropyl, cyclopentyl and cyclohexyl. The lower alkoxy defined with respect to the substituents for A, B and C may be one derived from the above lower alkyl and examples thereof include methoxy, ethoxy, n-propoxy, isopropoxy, n-butoxy, isobutoxy and tert-butoxy, among which methoxy and ethoxy are preferable. Further, the halogen defined with respect thereto includes fluorine, chlorine and bromine.

The sulfonamide or sulfonic ester derivative represented by the general formula (I) may form a salt together with an acid or a base. The present invention also includes salts of the compounds (I). Examples of the salt with an acid include the salts with inorganic acids such as hydrogen chloride, hydrogen bromide and sulfuric acid, and those with organic acids such as butyric acid, lactic acid, succinic acid, fumaric acid, maleic acid, citric acid, benzoic acid, methanesulfonic acid and p-toluenesulfonic acid, while examples of the salt with a base include the salts with inorganic bases such as sodium, potassium and calcium and those with organic bases such as triethylamine, arginine and lysine.

It is needless to say that the present invention includes hydrates and optical isomers of these compounds, if they are present. Although the compounds of the present invention exhibit a high antitumor activity, the present invention also includes compounds which undergo metabolism such as oxidation, reduction, hydrolysis or conjugation in vivo to exhibit an antitumor activity. Further, the present invention also includes compounds which undergo metabolism such as oxidation, reduction or hydrolysis in vivo to form the compounds of the present invention.

Although the compound (I) of the present invention can be prepared by various processes, representative processes for the preparation of the compound (I) will now be described.

1) The compound (I) can be prepared by reacting a sulfonic acid represented by the general formula (II):

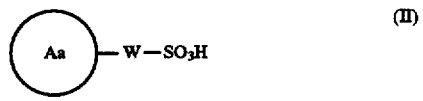

(wherein Aa represents a monocyclic or bicyclic aromatic ring which may have a protected or unprotected substituent; and W is as defined above) or a reactive derivative thereof with a compound represented by the general formula (III):

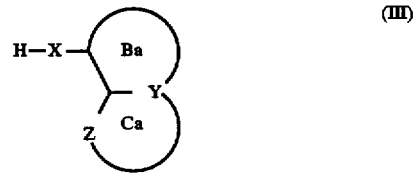

(wherein Ba represents a six-membered unsaturated hydrocarbon ring or six-membered heterocycle containing one nitrogen atom as the heteroatom, each of which may have a protected or unprotected substituent; Ca represents a five-membered heterocycle containing one or two nitrogen atoms which may have a protected or unprotected substituent; and X, Y and Z are each as defined above).

The reactive derivative of the sulfonic acid (II) may be any conventional one and examples thereof include sulfonyl halide, sulfonic anhydride and N-sulfonylimidazolide, among which sulfonyl halide is particularly preferable. Although the solvent to be used in the above reaction is not particularly limited, a solvent in which the starting materials are soluble and which is little reactive with the materials is preferably used. Examples of such a solvent include pyridine, tetrahydrofuran, dioxane, benzene, ethyl ether, dichloromethane, dimethylformamide and mixtures of two or more of them. When an acid is liberated with the progress of the reaction like in the case of using a halide of the sulfonic acid, it is preferable that the reaction be conducted in the presence of a suitable deacidifying agent. From this standpoint, the use of a basic solvent such as pyridine is particularly preferable. When a neutral solvent is used, a basic substance such as an alkali carbonate or organic tertiary amine may be added. Of course, the solvent usable in the reaction is not limited to those described above. Although the reaction generally proceeds at room temperature, it may be conducted under cooling or heating at need. The reaction time is generally 10 minutes to 20 hours and may be arbitrarily selected in view of the types of the starting materials and reaction temperature.

When the obtained product has a protected amino or hydroxyl group, if necessary, the product can be converted into a sulfonamide derivative or a sulfonic ester derivative (I) having a free hydroxyl or amino group by a conventional deblocking method such as treatment with acid or alkali or catalytic reduction.

2) The compound (I) can be prepared by reacting a compound represented by the general formula (IV):

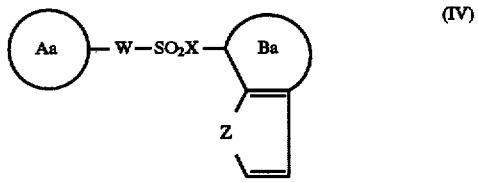

(IV)

(wherein Aa, Ba, W, X and Z are each as defined above) with a halogenating agent. Examples of the halogenating agent include N-chlorosuccinimide, N-bromosuccinimide, 1,3-dibromo-5,5-dimethylhydantoin, N-bromoacetamide, chlorine and bromine. Although the solvent to be used in the reaction is not particularly limited, examples of the solvent include chloroalkanes such as dichloromethane, chloroform and carbon tetrachloride; chlorinated aromatic compounds such as chlorobenzene and dichlorobenzene; and water-soluble solvents such as dimethylformamide, dioxane, pyridine and acetonitrile. The reaction temperature generally ranges from −50° to 100° C., though it varies depending upon the types of the halogenating agent and the substrate.

When the obtained product has a protected amino or hydroxyl group, if necessary, the product can be converted into a sulfonamide derivative or a sulfonic ester derivative (I) having a free hydroxyl or amino group by a conventional deblocking method such as treatment with acid or alkali or catalytic reduction.

3) The compound (I) can be prepared by reacting a compound represented by the general formula (V):

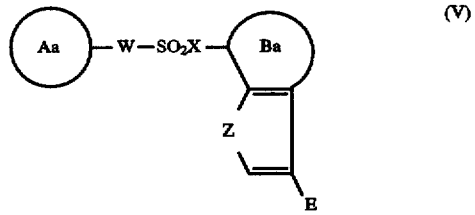

(V)

(wherein Aa, Ba, W, X and Z are each as defined above; and E represents a substituent convertible into a cyano group through dehydration) with a dehydrating agent. Examples of such a substituent that convertible into a cyano group through dehydration include (hydroxyimino) methyl and carbamoyl.

Alternatively, the oxime or acid amide may be prepared from the starting material aldehyde or carboxylic acid and may be reacted with a dehydrating agent without being isolated. The dehydrating agent may be any one conventionally used in the synthesis of nitriles and examples thereof include acetic anhydride, thionyl chloride, phosphorus oxychloride, selenium dioxide and 1,3-dicyclohexylcarbodiimide. Although the solvent to be used in the reaction is not particularly limited, a solvent in which the starting materials are soluble and which is little reactive with them is preferably used, and examples of such a solvent include pyridine, ethyl ether, benzene, dimethylformamide, carbon tetrachloride, acetonitrile, tetrahydrofuran and mixtures of two or more of them. The reaction temperature generally ranges from −50° to 150° C., though it varies depending upon the types of the dehydrating agent and the substrate.

When the obtained product has a protected amino or hydroxyl group, if necessary, the product can be converted into a sulfonamide derivative or a sulfonic ester derivative (I) having a free hydroxyl or amino group by a conventional deblocking method such as treatment with acid or alkali or catalytic reduction.

4) The compound (I) can be prepared by reacting a compound represented by the general formula (VI):

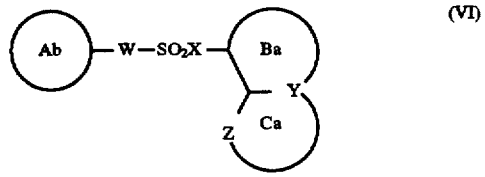

(VI)

(wherein Ab represents a monocyclic or bicyclic aromatic ring which has a substituent convertible into an amino group through reduction and may have a protected or unprotected substituent; and Ba, Ca, W, X, Y and Z are each as defined above) with a reducing agent. The substituent convertible into an amino group through reduction includes nitro, nitroso, hydroxyamino and azo groups.

Although the reduction can be conducted by any conventional process for reducing a nitro group, it is preferably conducted by catalytic reduction using palladium-carbon or platinum oxide as the catalyst or reduction using an acid together with zinc, iron or tin. The catalytic reduction is generally conducted in an organic solvent such as methanol, tetrahydrofuran or dimethylformamide under normal or elevated pressure.

When the obtained product has a protected hydroxyl group, if necessary, the product can be converted into a sulfonamide derivative or a sulfonic ester derivative (I) having a free hydroxyl group by a conventional deblocking method such as treatment with acid or alkali or catalytic reduction.

5) The compound (I) can be prepared by reacting a compound represented by the general formula (VII):

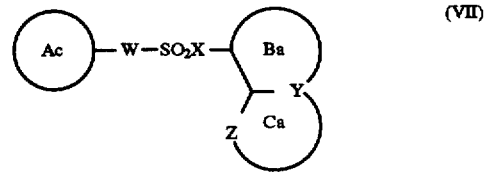

(VII)

(wherein Ac represents a monocyclic or bicyclic aromatic ring which has a leaving group on the ring or the substituent and may have a protected or unprotected substituent; and Ba, Ca, W, X, Y and Z are each as defined above) with a nucleophile. The leaving group includes halogen, methanesulfonyloxy and p-toluenesulfonyloxy groups. The nucleophile includes amines, alcohols and thiols. The alcohol or thiol may be used in the form of a salt with an alkali metal or the like. Although the solvent to be used in the reaction is not particularly limited, a solvent in which the starting materials are soluble and which is little reactive with them is preferably used. Examples of such a solvent include tetrahydrofuran, dioxane, dimethylformamide and water. The reaction temperature generally ranges from −50° to 150° C., though it varies depending upon the type of the substrate.

When the obtained product has a protected amino or hydroxyl group, if necessary, the product can be converted into a sulfonamide derivative or a sulfonic ester derivative (I) having a free hydroxyl or amino group by a conventional deblocking method such as treatment with acid or alkali or catalytic reduction.

Then, the preparation of the starting compound (II) and reactive derivative thereof and (III) will be described.

The starting compound (II) and reactive derivative thereof include both of known compounds and novel compounds. These novel compounds can be each prepared by applying one of the processes which have already been reported for the preparation of known compounds or combining two or more of the processes. For example, processes described in Chem. Ber., 90, 841 (1957), J. Med. Chem., 6, 307 (1963), J. Chem. Soc. (c), 1968, 1265, Chem. Lett., 1992, 1483, J. Am. Chem. Soc., 59, 1837 (1937), J. Med. Chem., 23, 1376 (1980), J. Am. Chem. Soc., 70, 375 (1948) and J. Am. Chem. Soc., 78, 2171 (1956) can be applied to the preparation of novel sulfonyl chlorides.

The starting compound (III) also includes both of known compounds and novel compounds. The starting compound (III) wherein H—X— is amino ($H_2N$—) can be prepared by reducing the corresponding nitro compound by a conventional process for reducing a nitro group. This reduction is preferably conducted catalytically with palladium-carbon as the catalyst or by using powdery zinc and hydrochloric acid. The catalytic reduction can be generally conducted in an organic solvent such as methanol, tetrahydrofuran or dimethylformamide under normal or elevated pressure.

The starting compound (III) wherein H—X— is hydroxyl (HO—) can be prepared by diazotizing the above amino compound and hydrolyzing the resulting diazo compound.

When the starting compound is novel compound, it can be prepared by applying one of the processes which have already been reported for the preparation of known compounds, or combining two or more of such processes. For example, a novel starting compound can be prepared by applying the process described in Can. J. Chem., 42, 1235 (1964), Chem. Abst., 59, 8855f (1963) or Tetrahedron Lett., 30, 2129 (1989) through the following reaction routes:

reaction scheme 1

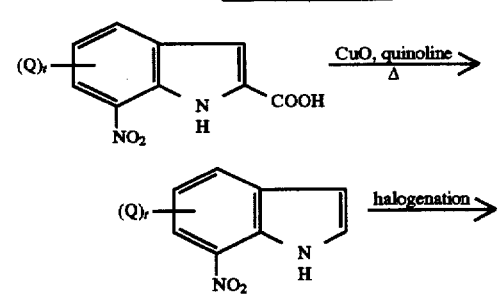

-continued reaction scheme 1

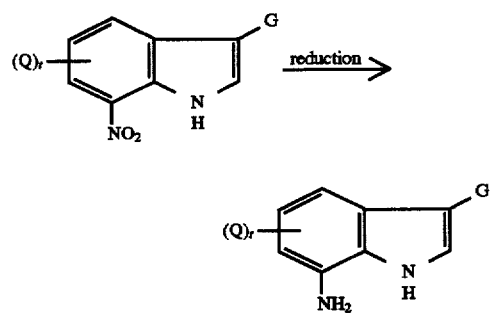

wherein Qs are the same or different from each other and each represents a substituent; G represents halogen and t is an integer of 0 to 2.

reaction scheme 2

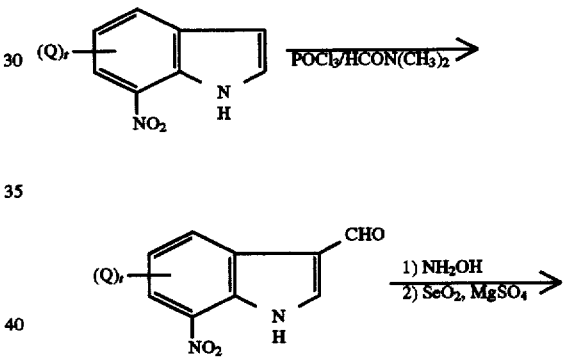

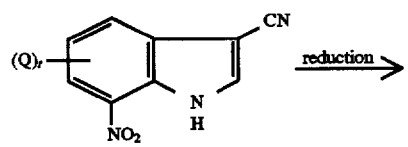

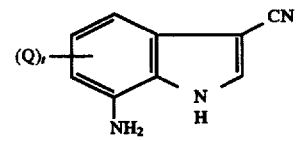

wherein Q and t are each as defined above.

reaction scheme 3

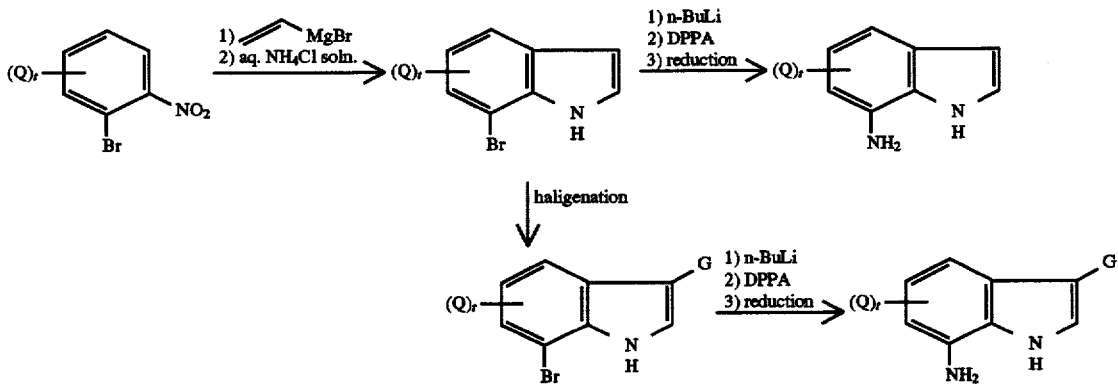

wherein Q, G and t are each as defined above; and DPPA refers to diphenylphosphorylazide.

reaction scheme 4

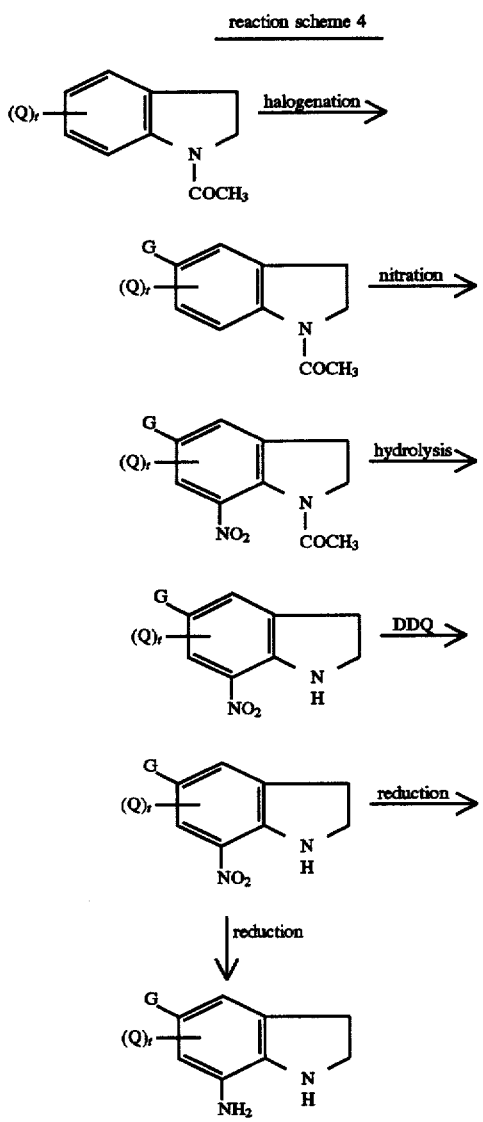

-continued
reaction scheme 4

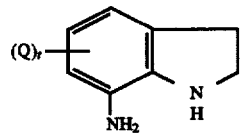

wherein Q, G and t are each as defined above; and DDQ refers to 2,3-dichloro-5,6-dicyano-1,4-benzoquinone.

When the compound of the present invention is used as a drug, it is administered orally or parenterally. Although the dose thereof varies depending upon the extent of symptom; the age, sex, weight and sensitivity of a patient; the method, timing and interval of administration; the properties, dispensing and type of pharmaceutical preparation; the type of an active ingredient and so forth and therefore is not particularly limited, the dose per adult a day is 10 to 6000 mg, preferably about 50 to 4000 mg, still preferably 100 to 3000 mg, which is generally administered in 1 to 3 portions a day.

A solid preparation for oral administration is prepared by adding a filler and, if necessary, a binder, disintegrator, lubricant, color and/or corrigent to an active ingredient and shaping the obtained mixture into a tablet, coated tablet, granule, fine granule, powder or capsule by the conventional process.

Examples of the filler include lactose, corn starch, sucrose, glucose, sorbitol, crystalline cellulose and silicon dioxide; those of the binder include polyvinyl alcohol, ethylcellulose, methylcellulose, acacia, hydroxypropylcellulose and hydroxypropylmethylcellulose; those of the lubricant include magnesium stearate, talc and silica; those of the color include those authorized as pharmaceutical additives; and those of the corrigent include cocoa powder, menthol, aromatic powder, mentha oil, borneol and powdered cinnamon bark. Of course, the tablet and granule may be suitably coated with sugar, gelatin or the like, if necessary.

An injection is prepared by adding a pH regulator, buffer, suspending agent, solubilizing agent, stabilizer, isotonizing agent and/or preservative to an active ingredient at need and forming the obtained mixture into an injection for intravenous, subcutaneous or intramuscular administration by a conventional process. If necessary, the prepared injection may be freeze-dried by a conventional process.

Examples of the suspending agent include methylcellulose, Polysorbate 80, hydroxyethylcellulose, acacia, tragacanth powder, sodium carboxymethylcellulose and polyoxyethylene sorbitan monolaurate.

Examples of the solubilizing agent include polyoxyethylene hardened castor oil, Polysorbate 80, nicotinamide, polyoxyethylene sorbitan monolaurate, macrogol and ethyl ester of castor oil fatty acid.

Examples of the stabilizer include sodium sulfite and sodium metasulfite; and those of the preservative include methyl p-hydroxybenzoate, ethyl p-hydroxybenzoate, sorbic acid, phenol, cresol and chlorocresol.

Pharmacological Experimental Examples will now be described to illustrate the effect of the compound of the present invention, wherein 2-sulfanylamido-5-chloroquinoxaline (CQS: Japanese Patent Laid-Open No. 62-426), which is a known heterobicyclic sulfonamide, was used as the control for the evaluation of the effect.

EXPERIMENTAL EXAMPLE 1

In vitro Antitumor Test Against Colon 38 Cells (Mouse Colon Cancer Cells)

$2.5 \times 10^3$ (0.1 ml) of colon 38 cells suspended in RPMI1640 medium (a product of Sanko Junyaku) containing 10% of fetal bovine serum, penicillin (100 units/ml), streptomycin (100 µg/ml), mercaptoethanol ($5 \times 10^{-5}$M) and sodium pyruvate (1 mM) were inoculated in each well of a 96-well flat-bottomed microplate, and cultured in an incubator containing 5% of carbon dioxide at 37° C. for one day.

A test compound according to the present invention was dissolved in dimethyl sulfoxide in a concentration of 20 mg/ml and the resulting solution was diluted with 10% fetal bovine serum/RPMI1640 medium to a concentration of 200 µg/ml. The resulting solution was diluted with 10% fetal bovine serum/RPMI1640 medium to prepare 3-fold serial dilutions with the maximum concentration being 200 µg/ml. The obtained dilutions were each poured into the well of the above-described culture plate in an amount of 0.1 ml. The resulting plate was cultured at 37° C. in an incubator containing 5% of carbon dioxide for 3 days.

Thereafter, a solution of MTT[3-(4,5-dimethylthiazol-2-yl)-2,5-diphenyltetrazolium bromide] (having a concentration of 3.3 mg/ml) was added to each well in an amount of 0.05 ml. The resulting mixtures were further incubated for 2 hours. The supernatant was removed from each well by suction. Formed formazan was dissolved in 0.1 ml of dimethyl sulfoxide. The absorbance at 540 nm was determined with a microplate reader and the absorbance was taken as an index of the number of viable cells. The inhibitory ratio of the test compound was calculated according to the following formula to determine the $IC_{50}$ of the test compound, with the $IC_{50}$ referring to the concentration at which 50% of mouse colon 38 cells are inhibited:

$$\text{inhibitory ratio (\%)} = \frac{C - T}{C} \times 100$$

T: absorbance of well containing a test compound
C: absorbance of well containing no test compound
The $IC_{50}$ values thus determined are given in Tables 1-1 and 1-2.

TABLE 1-1

In vitro antitumor test against colon 38 cells

| Compd. (Ex. No.) | $IC_{50}$ (µg/ml) | Compd. (Ex. No.) | $IC_{50}$ (µg/ml) |
|---|---|---|---|
| 2 | 0.54 | 36 | 0.11 |
| 3 | 0.23 | 37 | 0.19 |
| 4 | 0.26 | 38 | 0.57 |
| 6 | 0.17 | 40 | 0.27 |
| 7 | 0.22 | 41 | 0.57 |
| 8 | 0.09 | 42 | 0.25 |
| 10 | 0.13 | 43 | 0.47 |
| 13 | 0.63 | 45 | 0.44 |
| 14 | 0.23 | 46 | 0.47 |
| 15 | 0.35 | 47 | 0.22 |
| 17 | 0.13 | 48 | 0.23 |
| 18 | 0.11 | 49 | 0.32 |
| 19 | 0.10 | 50 | 0.22 |
| 21 | 0.12 | 51 | 0.09 |
| 22 | 0.69 | 52 | 0.14 |
| 23 | 0.13 | 53 | 0.12 |
| 24 | 0.09 | 54 | 0.51 |
| 26 | 0.17 | 55 | 0.59 |
| 27 | 0.10 | 56 | 0.20 |
| 28 | 0.12 | 57 | 0.66 |
| 29 | 0.19 | 59 | 0.54 |
| 32 | 0.17 | 60 | 0.08 |
| 33 | 0.10 | 61 | 0.24 |
| 34 | 0.14 | 62 | 0.18 |
| 35 | 0.14 | 63 | 0.12 |

TABLE 1-2

In vitro antitumor test against colon 38 cells

| Compd. (Ex. No.) | $IC_{50}$ (µg/ml) | Compd. (Ex. No.) | $IC_{50}$ (µg/ml) |
|---|---|---|---|
| 64 | 0.23 | 74 | 0.36 |
| 65 | 0.20 | 75 | 0.28 |
| 67 | 0.87 | 77 | 0.17 |
| 68 | 0.57 | 78 | 0.26 |
| 69 | 0.47 | 79 | 0.09 |
| 70 | 0.42 | 80 | 0.19 |
| 71 | 0.23 | 81 | 0.25 |
| 72 | 0.15 | 83 | 0.27 |
| 73 | 0.11 | CQS | 2.0 |

EXPERIMENTAL EXAMPLE 2

In vivo Antitumor Test Against Colon 38 (Mouse Colon Cancer)

About 75 mg of colon 38 was subcutaneously transplanted to the flank of each $BDF_1$ mouse (aged 7 weeks, female). A test compound according to the present invention was suspended in a physiological saline containing 3.5% of dimethyl sulfoxide and 6.5% of Tween 80 and the obtained suspension was intraperitoneally administered to the mice in a predetermined dose once a day for 8 days from the next day of transplantation. On the other hand, only a physiological saline containing 3.5% of dimethyl sulfoxide and 6.5% of Tween 80 was intraperitoneally administered to the mice of the control group. The control group was composed of ten mice, while each treated group was composed of six mice.

On the 21st day after the transplantation, the tumor was extirpated from each mouse to determine its weight. The tumor growth inhibition ratio was determined by the following formula:

$$\text{Growth inhibition ratio (\%)} = \frac{C-T}{C} \times 100$$

T: average weight of tumor of the treated group
C: average weight of tumor of the control group
The results are given in Table 2.

TABLE 2

In vivo antitumor test against colon 38

| Compd. (Ex. No.) | Dose (mg/kg/day) | Growth inhibition ratio (%) | Survival rate on the day of judgement (the 21st day) |
|---|---|---|---|
| 3 | 50 | 94 | 100 |
| 10 | 50 | 94 | 100 |
| 17 | 50 | 94 | 100 |
| 29 | 50 | 97 | 100 |
| 42 | 50 | 98 | 100 |
| CQS | 200 | 53 | 100 |

EXPERIMENTAL EXAMPLE 3

In vivo Antitumor Test Against HCT116 (Human Colon Cancer)

HCT116 (5 to 8×10$^6$) was subcutaneously transplanted to the flank of each nude mouse (BALB/c-nu/nu, aged 7 to 8 weeks, female). A test compound according to the present invention was suspended in a physiological saline containing 3.5% of dimethyl sulfoxide and 6.5% of Tween 80 and the obtained suspension was intraperitoneally administered to the mice treated above once a day in a predetermined dose for 4 days after the time at which the tumor volume had increased to about 100 mm$^3$, which was about 7 days after the transplantation. On the other hand, only a physiological saline containing 3.5% of dimethyl sulfoxide and 6.5% of Tween 80 was intraperitoneally administered to the mice of the control group. The control group was composed of ten mice, while each treated group was composed of five mice. On the 21st day after the initiation of administration, the tumor was extirpated from each mouse to determine its weight. The tumor growth inhibition ratio was determined by the following formula:

$$\text{Growth inhibition ratio (\%)} = \frac{C-T}{C} \times 100$$

T: average weight of tumor of the treated group
C: average weight of tumor of the control group
The results are given in Table 3.

TABLE 3

In vivo antitumor test against HCT116

| Compd. (Ex. No.) | Dose (mg/kg/day) | Growth inhibition ratio (%) | Survival rate on the day of judgement (the 21st day) |
|---|---|---|---|
| 4 | 100 | 97 | 100 |
| 19 | 50 | 88 | 100 |
| 21 | 100 | 95 | 100 |
| 23 | 100 | 87 | 100 |
| 28 | 100 | 77 | 100 |
| 29 | 100 | 80 | 100 |

TABLE 3-continued

In vivo antitumor test against HCT116

| Compd. (Ex. No.) | Dose (mg/kg/day) | Growth inhibition ratio (%) | Survival rate on the day of judgement (the 21st day) |
|---|---|---|---|
| 33 | 50 | 74 | 100 |
| 37 | 100 | 93 | 100 |
| 46 | 50 | 84 | 100 |
| 53 | 50 | 86 | 100 |
| 72 | 100 | 87 | 100 |
| 73 | 50 | 78 | 100 |
| CQS | 200 | 33 | 100 |

As apparent from the results of the above Experimental Examples, the compounds of the present invention exhibit such an excellent antitumor activity as to be useful as an antitumor agent.

EXAMPLE

Preparative Examples with respect to the preparation of the starting compounds used in preparing the compounds of the present invention and Examples with respect to the representative compounds according to the present invention will now be described, though the present invention is not limited to them.

PREPARATIVE EXAMPLE 1

7-Bromo-1H-indole

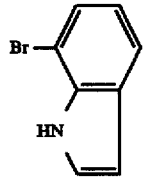

A 1.0M solution (100 ml) of vinylmagnesium bromide (100 mmol) in tetrahydrofuran was added to 250 ml of a solution of 5.05 g (25 mmol) of 2-bromonitrobenzene in tetrahydrofuran at −40° C. in a nitrogen atmosphere. The resulting mixture was stirred as such for 40 minutes and poured into 500 ml of a saturated aqueous solution of ammonium chloride. The obtained mixture was extracted with ethyl ether. The organic phase was dried over magnesium sulfate and concentrated. The residue was purified by silica gel column chromatography to give 2.89 g of the title compound.

$^1$H-NMR(DMSO-d$_6$) δ(ppm): 6.56(1H, dd, J=2.9, 1.8 Hz), 6.94(1H, t, J=7.8 Hz), 7.30(1H, d, J=7.8 Hz), 7.40(1H, t, J=2.9Hz), 7.56(1H, d, J=7.8 Hz), 11.16–11.46(1H, br m)

PREPARATIVE EXAMPLE 2

7-Amino-1H-indole

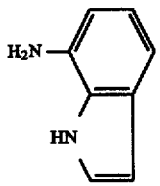

A 2.5M solution (16.5 ml) of n-butyllithium (41.3 mmol) in hexane was dropped into 50 ml of a solution of 2.70 g (13.8 mmol) of the compound prepared in Preparative Example 1 in tetrahydrofuran at −70° C. in a nitrogen atmosphere. The obtained mixture was stirred at −70° C. for 15 minutes and at −20° to −10° C. for 30 minutes. The resulting mixture was cooled to −70° C. again, followed by the dropwise addition of 3.9 ml (18 mmol) of diphenylphosphoryl azide. The obtained mixture was stirred at −70° C. for one hour and at −40° C. for one hour. 22.3 ml of a 3.4M solution of sodium bis(2-methoxyethoxy)aluminum hydride (75.8 mmol) in toluene was added to the resulting mixture at −40° C. The obtained mixture was stirred at −30° to −20° C. for 30 minutes and at room temperature for 30 minutes, followed by the addition of a phosphate buffer of pH7.0. The resulting mixture was filtered to remove insolubles and the filtrate was extracted with ethyl ether. The organic phase was washed with a saturated aqueous solution of sodium hydrogencarbonate and a saturated aqueous solution of common salt successively, dried over magnesium sulfate and concentrated. The obtained residue was purified by silica gel column chromatography to give 1.29 g of the title compound.

$^1$H-NMR(DMSO-d$_6$) δ(ppm): 5.01(2H, br s), 6.25–6.33 (2H, m), 6.70(1H, dd, J=7.9, 7.3 Hz), 6.78(1H, dd, J=7.9, 0.7 Hz), 7.23(1H, t, J=2.7 Hz), 10.48–10.72(1H, br m)

The following starting compounds were each prepared from 2-bromonitrobenzene derivatives in a similar manner to that of Preparative Examples 1 and 2.
7-Amino-4-methoxy-1H-indole,
7-Amino-4-bromo-1H-indole.

PREPARATIVE EXAMPLE 3

7-Bromo-3-chloro-4-methyl-1H-indole

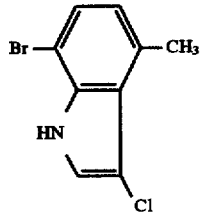

N-Chlorosuccinimide (4.0 g, 30.0 mmol) was added to 250 ml of an acetonitrile solution of 5.8 g (27.6 mmol) of 7-bromo-4-methyl-1H-indole prepared from 2-bromo-5-methylnitrobenzene in a similar manner to that of Preparative Example 1. The obtained mixture was stirred at room temperature overnight, followed by the addition of 50 ml of a 1N aqueous solution of sodium hydroxide. The resulting mixture was extracted with ethyl acetate. The organic phase was washed with water, dried over magnesium sulfate and concentrated. The obtained residue was purified by silica gel column chromatography to give 6.7 g of the title compound.

$^1$H-NMR(CDCl$_3$) δ(ppm): 2.74(3H, s), 6.75–7.26(3H, m), 8.23(1H, br s)

PREPARATIVE EXAMPLE 4

7-Amoni-3-chloro-4-methyl-1H-indole

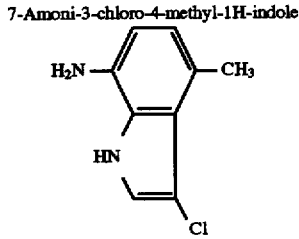

In a similar manner to that of Preparative Example 2, the title compound (2.6 g) was prepared from 6.37 g (26.1 mmol) of the compound prepared in Preparative Example 3.

$^1$H-NMR(CDCl$_3$) δ(ppm): 2.70(3H, s), 6.39–7.14(3H, m), 8.15(1H, br s)

PREPARATIVE EXAMPLE 5

4-Sulfamoylbenzenesulfonyl chloride

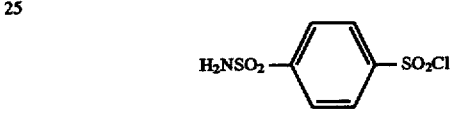

4-Aminobenzenesulfonamide (6.4 g, 37.2 mmol) was added to a mixture comprising 12.5 ml of water and 6.3 ml of concentrated hydrochloric acid. The obtained mixture was stirred, followed by the dropwise addition of a saturated aqueous solution of 2.56 g (37.1 mmol) of sodium nitrite at 0° C. or below. The obtained reaction mixture was added to an acetic acid solution saturated with sulfur dioxide (prepared by saturating 35 ml of acetic acid with sulfur dioxide and adding 1.5 g of cupric chloride dihydrate to the resulting solution) under cooling with ice and stirring. After 10 minutes, the reaction mixture was poured onto ice-water to give a precipitate. This precipitate was recovered by filtration, washed with water and dissolved in tetrahydrofuran. The obtained solution was dried over magnesium sulfate and concentrated to dryness to give 3.5 g of the title compound.

PREPARATIVE EXAMPLE 6

4-(Sulfamoylmethyl)benzenesulfonyl chloride

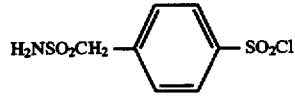

4-Nitrophenylmethanesulfonamide (5.0 g, 23.1 mmol) was suspended in 90% of acetic acid and hydrogenated in the presence of palladium-carbon at ordinary temperature under normal pressure. The resulting reaction mixture was filtered to remove the catalyst and the filtrate was concentrated to dryness to give 4.3 g of 4-aminophenylmethanesulfonamide. This product was added to a mixture comprising 40 ml of water and 4.1 ml of concentrated hydrochloric acid. The obtained mixture was stirred, followed by the dropwise addition of a saturated aqueous solution of 1.63 g (23.6 mmol) of sodium nitrite at 0° C. or below. The reaction mixture was added to an acetic acid solution saturated with sulfur dioxide (prepared by saturating 30 ml of acetic acid with sulfur dioxide and adding 0.97 g of cupric chloride dihydrate to the resulting solution) under cooling with ice and stirring. The resulting mixture was stirred at room temperature for 40 minutes and poured onto ice-water. The obtained mixture was saturated with common salt and extracted with ethyl acetate. The organic phase was dried over magnesium sulfate and concentrated to dryness to give 1.7 g of the title compound.

$^1$H-NMR(DMSO-d$_6$) δ(ppm): 4.26(2H, s), 7.32(2H, d, J=8.4 Hz), 7.59(2H, d, J=8.4 Hz)

The following compounds were each prepared in a similar manner to that of Preparative Example 5 or 6.

4-(N-Methylsulfamoyl)benzenesulfonyl chloride,
4-(N-Ethylsulfamoyl)benzenesulfonyl chloride,
4-(N-Methoxysulfamoyl)benzenesulfonyl chloride,
4-[(Methanesulfonamido)methyl]benzenesulfonyl chloride,
4-(N-Methylmethanesulfonamido)benzenesulfonyl chloride,
4-(1-Pyrrolidinylsulfonyl)benzenesulfonyl chloride,
4-(1-Pyrrolidinylcarbonyl)benzenesulfonyl chloride,
3-Cyanobenzenesulfonyl chloride,
4-(Methylsulfonyl)benzenesulfonyl chloride,
4-[(N-Methylmethanesulfonamido)methyl]benzenesulfonyl chloride.

PREPARATIVE EXAMPLE 7

3-Cyano-7-nitro-1H-indole

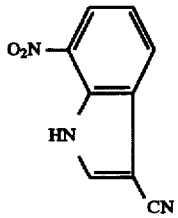

3-Formyl-7-nitro-1H-indole (10.15 g, 53.4 mmol) was dissolved in 150 ml of dimethylformamide, followed by the addition of 3.93 g (56.0 mmol) of hydroxylamine hydrochloride and 4.5 ml (55.6 mmol) of pyridine. The obtained mixture was stirred under heating at 70° to 80° C. for 2 hours, followed by the addition of 6.3 g (56.8 mmol) of selenium dioxide and about 5 g of magnesium sulfate. The obtained mixture was kept at 70° to 80° C. under heating for 2.5 hours and filtered to remove insolubles. The filtrate was concentrated. Water was added to the concentrate to precipitate crystals, which were recovered by filtration, washed with water and ethyl ether successively, and dissolved in a tetrahydrofuran/acetone mixture. The obtained mixture was filtered to remove insolubles, and the filtrate was concentrated, followed by the addition of ethyl acetate. The crystals thus precipitated were recovered by filtration to give 8.61 g of the title compound.

$^1$H-NMR(DMSO-d$_6$) δ(ppm): 7.48(1H, t, J=8.1 Hz), 8.17 (1H, d, J=8.1 Hz), 8.27(1H, d, J=8.1 Hz), 8.47(1H, s), 12.70–13.00(1H, br)

PREPARATIVE EXAMPLE 8

7-Amino-3-cyano-1H-indole

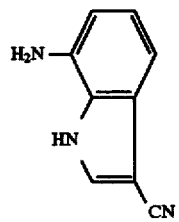

The compound (2.80 g, 15.0 mmol) prepared in Preparative Example 7 was suspended in 100 ml of methanol and hydrogenated in the presence of palladium-carbon at ordinary temperature under normal pressure. After the removal of the catalyst by filtration, the filtrate was concentrated to dryness to give 2.31 g of the title compound.

$^1$H-NMR(DMSO-d$_6$) δ(ppm): 5.32, 5.34(2H, s+s), 6.47 (1H, d, J=7.5 Hz), 6.81(1H, d, J=7.9 Hz), 6.94(1H, dd, J=7.9, 7.5 Hz), 8.13(1H, s), 11.55–11.90(1H, br)

PREPARATIVE EXAMPLE 9

7-Amino-3,4-dichloro-1H-indole

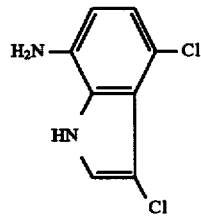

7-Bromo-4-chloro-1H-indole prepared from 2-bromo-5-chloronitrobenzene in a similar manner to that of Preparative Example 1 was chlorinated in a similar manner to that of Preparative Example 3. The obtained product was converted into the title compound by replacing the bromo group with an amino group in a similar manner to that of Preparative Example 2.

$^1$H-NMR(DMSO-d$_6$) δ(ppm): 5.26(2H, s), 6.29(1H, d, J=8.1 Hz), 6.74(1H, d, J=8.1 Hz), 7.45–7.51(1H, m), 11.08–11.27(1H, m)

7-Amino-4-tert-butyldimethylsilyloxy-3-chloro-1H-indole was prepared in a similar manner to that described above.

PREPARATIVE EXAMPLE 10

7-Amino-3-chloro-1H-indole

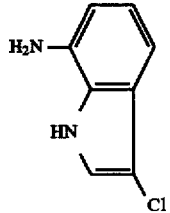

7-Nitro-1H-indole (1.076 g, 6.64 mmol) was dissolved in 30 ml of acetonitrile, followed by the addition of 920 mg (6.89 mmol) of N-chlorosuccinimide. The obtained mixture was stirred at room temperature for 36 hours. A saturated aqueous solution of sodium hydrogencarbonate was added to the resulting mixture to form a precipitate. The precipitate was recovered by filtration and washed with water to give 1.2 g of powdery 3-chloro-7-nitro-1H-indole. This powder (863 mg, 4.39 mmol) was suspended in 10 ml of ethanol, followed by the addition of 4.95 g (21.9 mmol) of stannous chloride dihydrate and 100 µl of concentrated hydrochloric acid. The obtained mixture was heated under reflux for 30 minutes, followed by the addition of a saturated aqueous solution of sodium hydrogencarbonate. The obtained mixture was filtered to remove insolubles. Ethyl acetate was added to the filtrate to conduct extraction. The organic phase was dried over magnesium sulfate and concentrated. The residue was purified by silica gel column chromatography to give 490 mg of the title compound.

The title compound was also prepared by hydrogenating 3-chloro-7-nitro-1H-indole in the presence of a platinum-carbon catalyst at ordinary temperature under normal pressure.

$^1$H-NMR(DMSO-$d_6$) δ(ppm): 5.14(2H, s), 6.36(1H, dd, J=7.5, 1.0 Hz), 6.68(1H, dd, J=7.9, 0.73 Hz), 6.81 (1H, dd, J=7.9, 7.5 Hz), 7.39(1H, d, J=2.7 Hz), 10.85(1H, br s)

PREPARATIVE EXAMPLE 11

4-(2-Sulfamoylethyl)benzenesulfonyl chloride

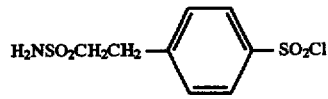

2-Phenylethanesulfonamide (1.3 g, 7.3 mmol) was added to 2.4 g (36.5 mmol) of chlorosulfonic acid under cooling with ice in 20 minutes. The obtained mixture was stirred at room temperature for 90 minutes and poured onto ice-water. The resulting mixture was extracted with ethyl acetate. The organic phase was washed with a saturated aqueous solution of sodium hydrogencarbonate and a saturated aqueous solution of common salt successively, dried over magnesium sulfate and distilled in a vacuum to remove the solvent, thus giving 1.6 g of the title compound.

$^1$H-NMR(DMSO-$d_6$) δ(ppm): 2.97–3.02(2H, m), 3.21–3.26(2H, m), 7.21(2H, d, J=8.4 Hz), 7.53(2H, d, J=8.4 Hz)

The following compounds were each prepared in a similar manner to that described above.

4-[2-(Methylsulfonyl)ethyl]benzenesulfonyl chloride,
4-[2-(N-Methylmethanesulfonamido)ethyl]benzenesulfonyl chloride,
4-[2-(Methanesulfonamido)ethyl]benzenesulfonyl chloride,
4-(N-Methylacetamido)benzenesulfonyl chloride.

PREPARATIVE EXAMPLE 12

5-Bromo-7-nitro-1H-indole

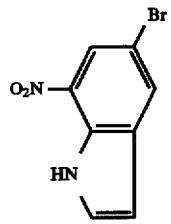

1-Acetyl-5-bromo-7-nitroindoline (5.05 g, 17.7 mmol) was added to a mixture comprising 6 ml of ethanol and 40 ml of 6N hydrochloric acid. The obtained mixture was heated under reflux for 3 hours, neutralized with sodium carbonate and extracted with ethyl acetate. The organic phase was washed with water, dried over magnesium sulfate and concentrated. The residue was purified by silica gel column chromatography to give 4.13 g of 5-bromo-7-nitroindoline. This compound (301 mg, 1.24 mmol) was added to 10 ml of toluene, followed by the addition of 580 mg (2.55 mmol) of 2,3-dichloro-5,6-dicyano-1,4-benzoquinone. The obtained mixture was refluxed by heating under stirring for 3.5 hours and filtered to remove insolubles. The filtrate was concentrated and the obtained residue was purified by silica gel column chromatography to give 252 mg of the title compound.

PREPARATIVE EXAMPLE 13

5-Bromo-3-formyl-7-nitro-1H-indole

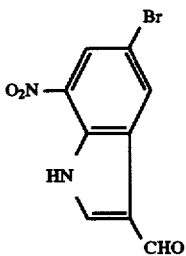

Phosphorus oxychloride (210 mg, 1.4 mmol) was added to 1.0 g (14 mmol) of dimethylformamide in a nitrogen atmosphere at 0° C. The obtained mixture was stirred for 30 minutes, followed by the addition of 240 mg (1.0 mmol) of the compound prepared in Preparative Example 12 at 0° C. The obtained mixture was stirred at 0° C. for 20 minutes and at 100° C. for 30 minutes, cooled with ice and poured onto ice-water. The resulting mixture was stirred for 30 minutes, while the pH of the mixture was kept at 7 to 8 by the addition of a 1N aqueous solution of sodium hydroxide. The precipitate thus formed was recovered by filtration and purified by silica gel column chromatography to give 239 mg of the title compound.

$^1$H-NMR(DMSO-$d_6$) δ(ppm): 8.31(1H, d, J=1.8 Hz), 8.55 (1H, s), 8.65(1H, d, J=1.8 Hz), 10.05(1H, s), 12.89(1H, br s)

PREPARATIVE EXAMPLE 14

7-Amino-5-bromo-3-cyano-1H-indole

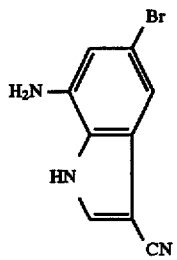

5-Bromo-3-cyano-7-nitro-1H-indole (214 mg, 0.8 mmol) prepared from the compound prepared in Preparative Example 13 in a similar manner to that of Preparative Example 7 was dissolved in a mixture comprising 10 ml of methanol and 10 ml of tetrahydrofuran and hydrogenated in the presence of platinum oxide at 3.0 kg/cm$^2$ of hydrogen. The catalyst was filtered out and the filtrate was concentrated to dryness to give 189 mg of the title compound.

$^1$H-NMR(DMSO-d$_6$) δ(ppm): 5.68–5.71(2H, m), 6.60 (1H, d, J=2.0 Hz), 6.91(1H, d, J=2.0 Hz), 8.16(1H, s)

PREPARATIVE EXAMPLE 15

3-Acetyl-7-amino-1H-indole

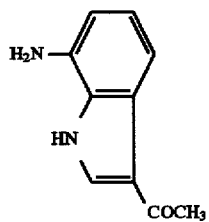

A 1.0M solution (11 ml) of dimethylaluminum chloride (11 mmol) in hexane was added to 50 ml of a solution of 1.2 g (7.5 mmol) of 7-nitro-1H-indole in dichloromethane at 0° C. in a nitrogen atmosphere, followed by the addition of 2.1 ml (29.5 mmol) of acetyl chloride at 0° C. The obtained mixture was stirred at room temperature for 4 hours, followed by the addition of a saturated aqueous solution of ammonium chloride. The precipitate thus formed was recovered by filtration and washed with hot ethanol sufficiently. The washings and the filtrate were combined and concentrated. Water was added to the residue and the resulting mixture was extracted with ethyl acetate. The organic phase was washed with a saturated aqueous solution of common salt, dried over magnesium sulfate and distilled in a vacuum to remove the solvent. The residue was purified by silica gel column chromatography to give 3-acetyl-7-nitro-1H-indole. This product was dissolved in 100 ml of methanol and hydrogenated in the presence of palladium-carbon at ordinary temperature under normal pressure. After the removal of the catalyst by filtration, the filtrate was concentrated to dryness to give 790 mg of the title compound.

EXAMPLE 1

N-(1H-Indol-7-yl)-4-nitrobenzenesulfonamide

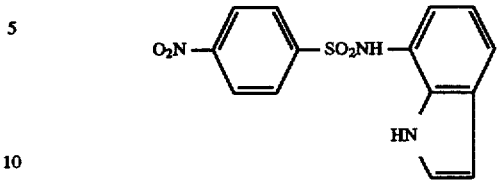

The compound (1.50 g, 11.3 mmol) prepared in Preparative Example 2 was dissolved in 40 ml of pyridine. 2.57 g (11.6 mmol) of 4-nitrobenzenesulfonyl chloride was added to the obtained solution at room temperature under stirring. The obtained mixture was stirred at room temperature overnight and distilled in a vacuum to remove the solvent. Ethyl acetate and 0.2N hydrochloric acid were added to the obtained residue. The organic phase was recovered, washed with water, dried over magnesium sulfate, and distilled in a vacuum to remove the solvent. The obtained residue was purified by silica gel column chromatography to give 3.50 g of the title compound.

$^1$H-NMR(DMSO-d$_6$) δ(ppm): 6.42(1H, dd, J=2.8, 2.0 Hz), 6.66(1H, d, J=7.6 Hz), 6.83(1H, dd, J=8.0, 7.6 Hz), 7.31(1H, dd, J=3.2, 2.8 Hz), 7.36(1H, d, J=8.0 Hz), 7.94–8.02(2H, m), 8.30–8.38(2H, m), 10.23(1H, s), 10.74–10.87(1H, m)

EXAMPLE 2

N-(3-Chloro-1H-indol-7-yl)-4-nitrobenzenesulfonamide

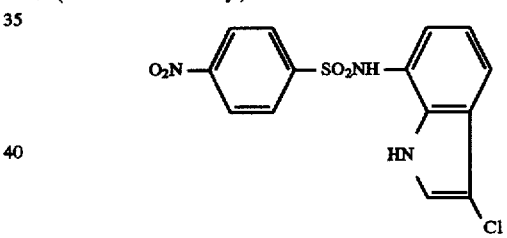

The compound (8.98 g, 28.3 mmol) prepared in Example 1 was dissolved in a mixture comprising 280 ml of dichloromethane and 7 ml of dimethylformamide, followed by the addition of 4.16 g (31.2 mmol) of N-chlorosuccinimide in a nitrogen atmosphere under stirring. The obtained mixture was stirred at room temperature for 1.5 hours, followed by the addition of 50 ml of water. The obtained mixture was concentrated to about 80 ml, followed by the addition of ethyl acetate and 0.2N hydrochloric acid. The organic phase was recovered, washed with a saturated aqueous solution of sodium hydrogencarbonate and a saturated aqueous solution of common salt successively, dried over magnesium sulfate, and distilled in a vacuum to remove the solvent. The obtained residue was purified by silica gel column chromatography to give 7.98 g of the title compound.

M.p.: 199.5° to 200.5° C. (recrystallized from chloroform)

$^1$H-NMR(DMSO-d$_6$) δ(ppm): 6.72(1H, d, J=7.6 Hz), 6.96 (1H, dd, J=8.0, 7.6 Hz), 7.31(1H, d, J=8.0 Hz), 7.47–7.53 (1H, m), 7.92–8.02(2H, m), 8.30–8.41(2H, m), 10.33(1H, s), 11.07–11.22(1H, m)

EXAMPLE 3

4-Amino-N-(3-chloro-1H-indol-7-yl)benzenesulfonamide

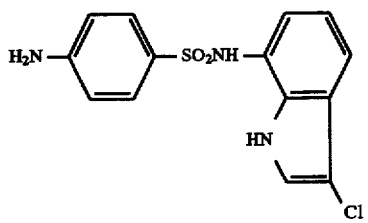

The compound (7.98 g, 22.7 mmol) prepared in Example 2 was dissolved in 220 ml of methanol. The obtained solution was refluxed by heating under stirring. 10 ml of concentrated hydrochloric acid and 7.40 g of powdery zinc were added to the resulting solution three times at intervals of 10 minutes. The obtained mixture was refluxed for 10 minutes, cooled, neutralized with a large excess of sodium hydrogencarbonate, and filtered to remove insolubles. The filtrate was concentrated and the obtained residue was dissolved in ethyl acetate. The obtained solution was washed with a saturated aqueous solution of sodium hydrogencarbonate, a 2N aqueous solution of sodium carbonate and a saturated aqueous solution of common salt successively, dried over magnesium sulfate and distilled in a vacuum to remove the solvent, thus giving 7.21 g of the title compound.

M.p.: 174.5° to 176° C. (recrystallized from ethanol-n-hexane)

$^1$-NMR(DMSO-d$_6$) δ(ppm): 5.97(2H, br s),6.48(2H, d, J=8.8 Hz), 6.88(1H, d, J=7.6 Hz), 6.95(1H, dd, J=8.0, 7.6 Hz), 7.19(1H, d, J=8.0 Hz), 7.36(2H, d, J=8.8 Hz), 7.46(1H, d, J=2.4 Hz), 9.56(1H, s), 10.86–10.98(1H, m)

EXAMPLE 4

N-(3-Chloro-1H-indol-7-yl)-4-(methanesulfon-amido)benzenesulfonamide

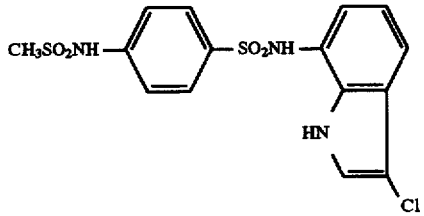

The compound (68 mg, 0.211 mmol) prepared in Example 3 was dissolved in 1 ml of pyridine, followed by the addition of 15 μl (0.194 mmol) of methanesulfonyl chloride. The obtained mixture was stirred at room temperature overnight, followed by the addition of an aqueous solution of sodium hydrogencarbonate. The obtained mixture was extracted with ethyl acetate. The organic phase was washed with dilute hydrochloric acid and water successively, dried over magnesium sulfate and concentrated. The obtained residue was purified by silica gel thin-layer chromatography to give 76 mg of the title compound.

M.p.: 213.5° to 214° C. (dec.) (recrystallized from ethanol-n-hexane)

$^1$H-NMR(DMSO-d$_6$) δ(ppm): 3.08(3H, s), 6.83(1H, d, J=7.5 Hz), 6.96(1H, dd, J=7.9, 7.7 Hz), 7.23(2H, d, J=8.8 Hz), 7.24(1H, d, J=7.5 Hz), 7.47(1H, d, J=2.7 Hz), 7.68(2H, d, J=8.8 Hz), 9.92(1H, br s), 10.38(1H, br s), 10.99(1H, br s)

EXAMPLE 5

4-Bromomethyl-N-(1H-indol-7-yl)benzenesulfonamide

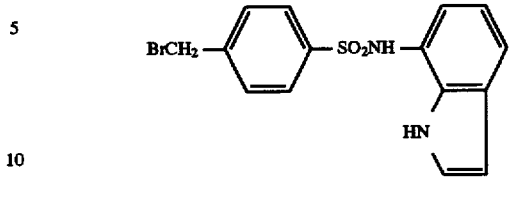

4-Bromomethylbenzenesulfonyl chloride was reacted with the compound prepared in Preparative Example 2 at room temperature in the presence of equimolar amounts of pyridine in tetrahydrofuran and the resulting reaction mixture was treated in the same manner as that of Example 1 to give the title compound.

$^1$H-NMR(DMSO-d$_6$) δ(ppm): 4.70(2H, s), 6.40(1H, dd, J=3.1, 1.1 Hz), 6.71(1H, ddd, J=7.4, 3.2, 0.92 Hz), 6.81(1H, ddd, J=8.1, 7.4, 0.92 Hz), 7.29–7.32(2H, m), 7.57(2H, d, J=8.2 Hz), 7.73(2H, d, J=8.4 Hz), 9.96(1H, br s), 10.75(1H, br s)

EXAMPLE 6

N-(1,3-Dihydro-2H-indol-2-on-7-yl)-4-methylbenzenesulfonamide

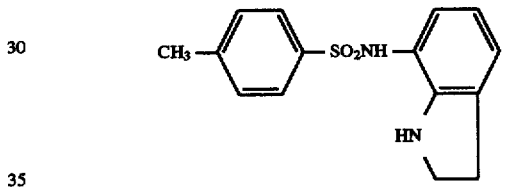

The title compound was prepared in a similar manner to that of Example 1.

M.p.: gradually began to decompose at about 246° C. and rapidly decomposed at 267° to 269° C. (recrystallized from dioxane).

EXAMPLE 7

3-Chloro-N-(3-chloro-1H-indol-7-yl)benzenesulfonamide

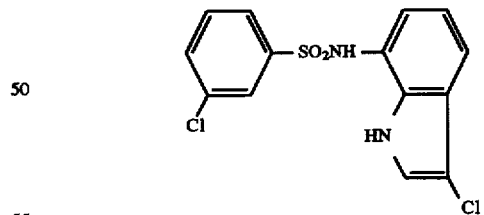

3-Chloro-N-(1H-indol-7-yl)benzenesulfonamide (2.18 g, 7.11 mmol) prepared in a similar manner to that of Example 1 was chlorinated in a similar manner to that of Example 2 to give 1.86 g of the title compound.

M.p.: 180° to 181° C. (recrystallized from dichloromethane-diisopropyl ether)

$^1$H-NMR(DMSO-d$_6$) δ(ppm): 6.73(1H, d, J=7.6 Hz), 6.97 (1H, dd, J=8.0, 7.6 Hz), 7.30(1H, d, J=8.0 Hz), 7.45–7.51 (1H, m), 7.51–7.76(4H, m), 10.09(1H, s), 11.02–11.18(1H, m)

EXAMPLE 8

4-Amino-N-(3,4-dichloro-1H-indol-7-yl)benzenesulfonamide

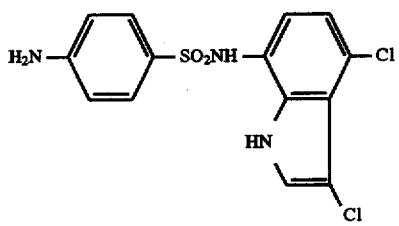

In a similar manner to that of Example 3, the title compound (2.03 g) was prepared from 2.43 g (6.29 mmol) of N-(3,4-dichloro-1H-indol-7-yl)-4-nitrobenzenesulfonamide prepared in a similar manner to that of Example 1.

M.p.: 205° to 206.5° C. (dec.) (recrystallized from ethanol-n-hexane)

$^1$H-NMR(DMSO-d$_6$) δ(ppm): 6.00(2H, s), 6.50(2H, d, J=8.4 Hz), 6.77(1H, d, J=8.0 Hz), 6.94(1H, d, J=8.0 Hz), 7.35(2H, d, J=8.4 Hz), 7.51–7.58(1H, m), 9.57(1H, s), 11.20–11.38(1H, m)

EXAMPLE 9

4-[N-(1H-Indol-7-yl)sulfamoyl]benzoic acid

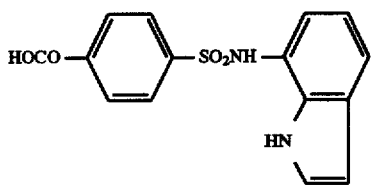

The title compound was prepared in a similar manner to that of Example 1.

$^1$H-NMR(DMSO-d$_6$) δ(ppm): 6.40(1H, dd, J=2.9, 1.9 Hz), 6.67(1H, d, J=7.5 Hz), 6.82(1H, dd, J=7.9, 7.5 Hz), 7.31(1H, dd, J=2.9, 2.7 Hz), 7.33(1H, d, J=7.9 Hz), 7.81–7.88(2H, m), 7.99–8.07(2H, m), 10.07(1H, s), 10.73–10.83(1H, m), 13.30–13.58(1H, br)

EXAMPLE 10

N-(3-Chloro-1H-indol-7-yl)-4-cyanobenzenesulfonamide

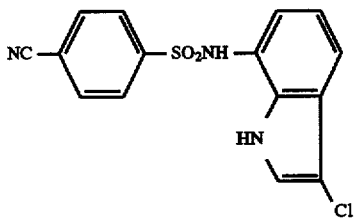

In a similar manner to that of Example 2, 76 mg of the title compound was prepared from 100 mg of 4-cyano-N-(1H-indol-7-yl)benzenesufonamide prepared in a similar manner to that of Example 1.

M.p.: 210° to 211° C. (recrystallized from ethyl acetate-n-hexane)

$^1$H-NMR(DMSO-d$_6$) δ(ppm): 6.71(1H, dd, J=7.6, 0.8 Hz), 6.96(1H, dd, J=8.0, 7.6 Hz), 7.30(1H, d, J=8.0 Hz), 7.48(1H, dd, J=2.4, 0.8 Hz), 7.82–7.90(2H, m), 7.97–8.05 (2H, m), 10.25(1H, s), 11.04–11.15(1H, m)

EXAMPLE 11

3-Chloro-N-(3-chloro-4-methoxy-1H-indol-7-yl)-benzenesulfonamide

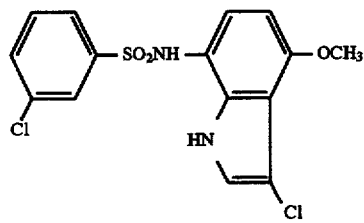

In a similar manner to that of Example 2, 52 mg of the title compound was prepared from 100 mg of 3-chloro-N-(4-methoxy-1H-indol-7-yl)benzenesulfonamide prepared in a similar manner to that of Example 1.

$^1$H-NMR(DMSO-d$_6$) δ(ppm): 3.79(3H, S), 6.37(1H, d, J=8.4 Hz), 6.45(1H, d, J=8.4 Hz), 7.24–7.31(1H, m), 7.48–7.77(4H, m), 9.76(1H, s), 11.06–11.17(1H, m)

EXAMPLE 12

3-Chloro-N-(3-chloro-4-hydroxy-1H-indol-7-yl)benzenesulfonamide

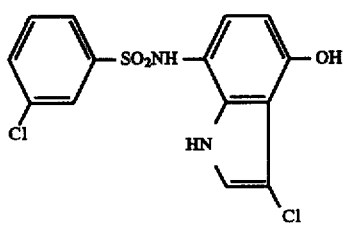

N-(4-tert-Butyldimethylsilyloxy-3-chloro-1H-indol-7-yl)-3-chlorobenzenesulfonamide (220 mg, 0.47 mmol) prepared in a similar manner to that of Example 1 was added to 2 ml of a mixture comprising a 40% aqueous solution of hydrogen fluoride and acetonitrile at a ratio of 1:10. The obtained mixture was stirred at room temperature overnight, followed by the addition of water. The obtained mixture was extracted with ethyl acetate. The organic phase was dried over magnesium sulfate and concentrated. The residue was purified by silica gel column chromatography to give 141 mg of the title compound.

$^1$H-NMR(DMSO-d$_6$) δ(ppm): 6.15(1H, dd, J=8.2, 1.5 Hz), 6.26(1H, d, J=8.2 Hz), 7.12(1H, s), 7.47–7.64(4H, m), 9.54(1H, s), 10.85(1H, s)

EXAMPLE 13

N-(1H-Indazol-7-yl)-4-methoxybenzenesulfonamide

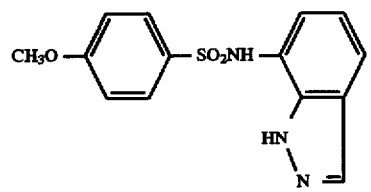

The title compound was prepared in a similar manner to that of Example 1.

M.p.: 155° to 156° C. (recrystallized from ethyl acetate-n-hexane)

¹H-NMR(DMSO-d₆) δ(ppm): 3.77(3H, s), 6.91–6.99(2H, m), 6.98–7.07(2H, m), 7.45–7.53(1H, m), 7.64–7.74(2H, m), 8.01–8.07(1H, m), 9.97(1H, s), 12.61–12.72(1H, m)

EXAMPLE 14

6-Chloro-N-(3-chloro-1H-indol-7-yl)-3-pyridinesulfonamide

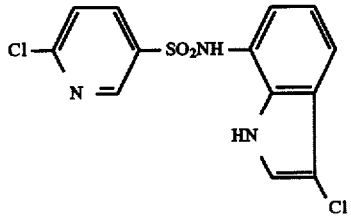

6-Chloro-3-pyridinesulfonyl chloride was reacted with the compound prepared in Preparative Example 2 in a similar manner to that of Example 1 to give 6-chloro-N-(1H-indol-7-yl)-3-pyridinesulfonamide and this product was chlorinated in a similar manner to that of Example 2 to give the title compound.

¹H-NMR(DMSO-d₆) δ(ppm): 6.73(1H, d, J=7.7 Hz), 6.97 (1H, dd, J=7.9, 7.7 Hz), 7.30(1H, d, J=7.9 Hz), 7.46(1H, d, J=2.6 Hz), 7.67(1H, d, J=8.4 Hz), 8.03(1H, dd, J=8.4, 2.6 Hz), 8.62(1H, d, J=2.6 Hz), 10.18–10.34(1H, br), 11.06–11.17(1H, m)

EXAMPLE 15

N-(3-Chloro-1H-indol-7-yl)-4-(methylthiomethyl)benzenesulfonamide

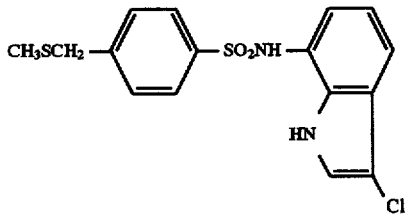

The compound (1.97 g, 5.37 mmol) prepared in Example 5 was dissolved in 10 ml of tetrahydrofuran, followed by the addition of 10 ml of a 15% aqueous solution of sodium methylthiolate (39.4 mmol) and a catalytic amount of methyltrioctylammonium chloride at room temperature. The obtained mixture was stirred overnight, followed by the addition of 20 ml of water. The obtained mixture was extracted with ethyl acetate. The organic phase was washed with water, dried over magnesium sulfate and concentrated. The residue was purified by silica gel column chromatography to give 1.51 g of N-(1H-indol-7-yl)-4-(methylthiomethyl)benzenesulfonamide. This product was chlorinated in a similar manner to that of Example 2 to give 839 mg of the title compound.

¹H-NMR(DMSO-d₆) δ(ppm): 1.87(3H, s), 3.70(2H, s), 6.77(1H, dd, J=7.6, 2.1 Hz), 6.94(1H, dd, J=7.9, 7.7 Hz), 7.24(1H, d, J=7.9 Hz), 7.42(2H, d, J=8.2 Hz), 7.47(1H, d, J=2.6 Hz), 7.67(2H, d, J=8.4 Hz), 9.96(1H, br s), 11.01(1H, br s)

EXAMPLE 16

3-Chloro-N-(3-formyl-1H-indol-7-yl)benzenesulfonamide

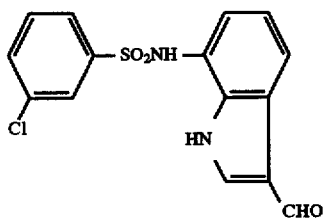

Phosphorus oxychloride (1.3 ml, 13.9 mmol) was dropped into 14.5 ml of dimethylformamide at 10° C. or below in a nitrogen atmosphere under stirring. The obtained mixture was stirred at about 5° C. for 30 minutes. 2.50 g (8.15 mmol) of 3-chloro-N-(1H-indol-7-yl)benzenesulfonamide prepared in a similar manner to that of Example 1 was added to the resulting mixture in three portions. The obtained mixture was further stirred at about 5° C. for 30 minutes, followed by the addition of 200 ml of chilled water. The pH of the reaction mixture was adjusted to about 14 with a 1N aqueous solution of sodium hydroxide, then to about 2 with 1N hydrochloric acid. The resulting mixture was extracted with ethyl acetate. The organic phase was washed with a saturated aqueous solution of common salt, dried over magnesium sulfate and concentrated. The residue was purified by silica gel column chromatography to give 1.45 g of the title compound.

¹H-NMR(DMSO-d₆) δ(ppm): 6.70(1H, dd, J=7.6, 0.8 Hz), 7.06(1H, dd, J=8.0, 7.6 Hz), 7.51–7.75(4H, m), 7.93 (1H, d, J=8.0 Hz), 8.22–8.28(1H, m), 9.93(1H, s), 10.17(1H, s), 11.86–11.98(1H, m)

EXAMPLE 17

3-Chloro-N-(3-cyano-1H-indol-7-yl)benzenesulfonamide

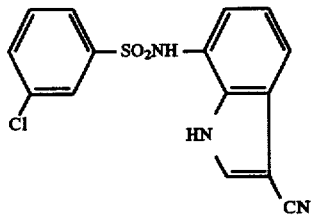

Hydroxylamine hydrochloride (274 mg, 3.94 mmol) and pyridine (0.32 ml, 3.96 mmol) were added to a solution (18 ml) of 1.20 g (3.58 mmol) of the compound prepared in Example 16 in dimethylformamide at 70° to 80° C. under stirring. The obtained mixture was stirred as such for 2.5 hours, followed by the addition of 437 mg (3.94 mmol) of selenium dioxide and about 100 mg of powdery magnesium sulfate. The obtained mixture was further stirred at that temperature for 2 hours and distilled in a vacuum to remove the solvent. Ethyl acetate was added to the residue and the resulting mixture was filtered to remove insolubles. The filtrate was washed with 0.1N hydrochloric acid and a saturated aqueous solution of common salt successively, dried over magnesium sulfate and distilled in a vacuum to remove the solvent. The residue was purified by silica gel column chromatography to give 678 mg of the title compound.

M.p.: 204.5° to 205° C. (recrystallized from ethyl acetate-n-hexane)

$^1$H-NMR(DMSO-d$_6$) δ(ppm): 6.71(1H, d, J=7.6 Hz), 7.08 (1H, dd, J=8.0, 7.6 Hz), 7.47(1H, d, J=8.0 Hz), 7.50–7.76 (4H, m), 8.17–8.25(1H, m), 10.21(1H, s), 11.92–12.09(1H, m)

EXAMPLE 18

6-Chloro-N-(3-cyano-1H-indol-7-yl)-3-pyridinesulfonamide

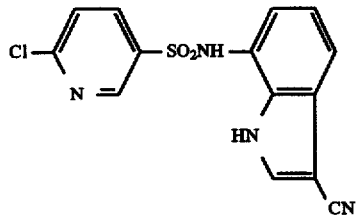

The title compound was prepared in a similar manner to that of Example 1.

$^1$H-NMR(DMSO-d$_6$) δ(ppm): 6.77(1H, d, J=7.9 Hz), 7.12 (1H, t, J=7.9 Hz), 7.50(1H, d, J=7.9 Hz), 7.72(1H, d, J=8.4Hz), 8.06(1H, dd, J=8.4, 2.6 Hz), 8.23(1H, d, J=2.6 Hz), 8.65(1H, d, J=2.6 Hz), 10.34–10.48(1H, br), 11.98–12.12(1H, m)

EXAMPLE 19

N-(3-Chloro-1H-indol-7-yl)-4-sulfamoylbenzenesulfonamide

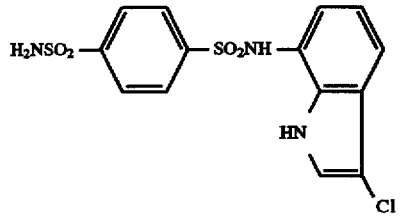

The compound (767 mg, 3.0 mmol) prepared in Preparative Example 5 was reacted with the compound. (264 mg, 2.0 mmol) prepared in Preparative Example 2 in a similar manner to that of Example 1 and the obtained reaction mixture was treated in a similar manner to that of Example 1. 445 mg of N-(1H-indol-7-yl)-4-sulfamoylbenzenesulfonamide was obtained. This product was chlorinated in a similar manner to that of Example 2 to give 349 mg of the title compound.

M.p.: began to blacken partially at about 220° C. and decompose gradually at about 240° C. (recrystallized from ethanol-n-hexane)

$^1$H-NMR(DMSO-d$_6$) δ(ppm): 6.75(1H, d, J=7.6 Hz), 6.96 (1H, dd, J=8.0, 7.6 Hz), 7.29(1H, d, J=7.6 Hz), 7.50(1H, d, J=2.8 Hz), 7.58(2H, s), 7.90–7.98(4H, m), 10.23(1H, s), 11.07–11.17(1H, m)

EXAMPLE 20

3-Chloro-N-(8-imidazo[1,2-a]pyridinyl)benzenesulfonamide hydrochloride

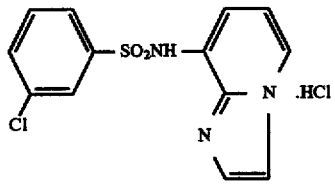

2,3-Diaminopyridine (1.97 g, 18 mmol) was dissolved in a tetrahydrofuran/water mixture, followed by the addition of a solution of 1.90 g (9.0 mmol) of 3-chlorobenzenesulfonyl chloride in tetrahydrofuran. The obtained mixture was stirred at room temperature overnight and concentrated, followed by the addition of water and dichloromethane. The organic phase was recovered and put in a vessel and the inside wall of the vessel was scratched to precipitate crystals. The formed crystals were recovered by filtration to give 1.41 g of N-(2-amino-3-pyridinyl)-3-chlorobenzenesulfonamide. 530 mg (1.87 mmol) of the crystals was dissolved in methanol, followed by the addition of a 40% aqueous solution of chloroacetaldehyde (367 mg, 1.87 mmol). The obtained mixture was heated under reflux for 4 hours and concentrated to dryness. A small amount of methanol was added to the residue and the obtained mixture was filtered to give 373 mg of the title compound as a crystal.

M.p.: began to gradually decompose at about 210° C. (recrystallized from ethanol)

EXAMPLE 21

N-(3,4-Dichloro-1H-indol-7-yl)-4-sulfamoylbenzenesulfonamide

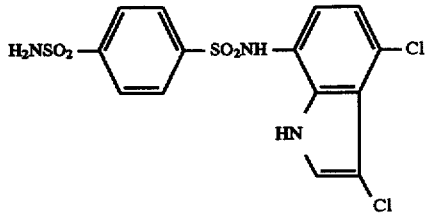

In a similar manner to that of Example 1, 429 mg (1.68 mmol) of the compound prepared in Preparative Example 5 was reacted with 250 mg (1.24 mmol) of the compound prepared in Preparative Example 9 and the reaction mixture was treated to give 200 mg of the title compound.

M.p.: began to discolor at about 282° C. and decomposed gradully (recrystallized from ethanol-ethyl ether)

$^1$H-NMR(DMSO-d$_6$) δ(ppm): 6.62(1H, d, J=8.1 Hz), 6.95 (1H, d, J=8.1 Hz), 7.53–7.62(3H, m), 7.87–7.99(4H, m), 10.17–10.33(1H, br), 11.44–11.56(1H, m)

EXAMPLE 22

N-(3-Chloro-1H-indol-7-yl)-4-(methylthio)benzenesulfonamide

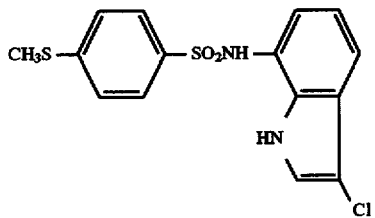

The title compound was prepared in a similar manner to that of Examples 1 and 2.

$^1$H-NMR(DMSO-d$_6$) δ(ppm): 2.48(3H, s),6.82(1H, dd, J=7.9, 1.5 Hz), 6.96(1H, dd, J=8.1, 7.5 Hz), 7.25(1H, dd, J=7.9, 0.92 Hz), 7.33(2H, d, J=8.8 Hz), 7.49(1H, d, J=2.7 Hz), 7.62(2H, d, J=8.6 Hz), 9.96(1H, br s), 11.02(1H, br s)

EXAMPLE 23

N-(3-Chloro-1H-indol-7-yl)-4-(methylsulfonyl)benzenesulfonamide

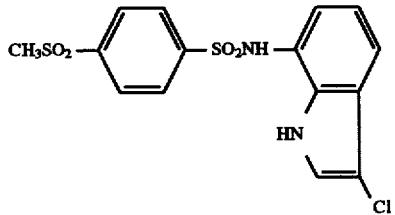

The compound (54.2 mg, 0.154 mmol) prepared in Example 22 was dissolved in a mixture comprising 2 ml of methanol and 1.2 ml of water, followed by the addition of 30 mg of ammonium molybdate tetrahydrate and 0.6 ml of 30% aqueous hydrogen peroxide. The obtained mixture was stirred overnight, followed by the addition of water. The resulting mixture was extracted with ethyl acetate. The organic phase was washed with water, dried over magnesium sulfate and concentrated. The residue was purified by silica gel column chromatography to give 29.4 mg of the title compound.

M.p.: began to discolor at about 250° C. and decomposed at 264° to 266° C. (recrystallized from ethanol-n-hexane)

$^1$H-NMR(DMSO-d$_6$) δ(ppm): 3.28(3H, S), 6.75(1H, d, J=7.7 Hz), 6.97(1H, dd, J=7.9, 7.7 Hz), 7.30(1H, d, J=8.1 Hz), 7.50(1H, d, J=2.7 Hz), 7.97(2H, d, J=8.2 Hz), 8.09(2H, d, J=8.4 Hz), 10.29(1H, br s), 11.12(1H, br s)

EXAMPLE 24

N-(3-Chloro-1H-indol-7-yl)-4-(methylsulfinyl)benzenesulfonamide

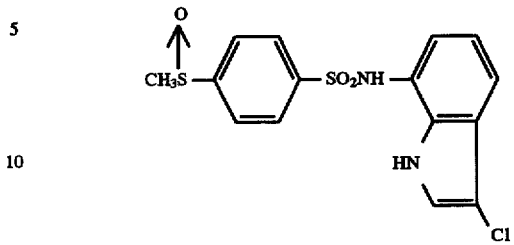

The compound (19.9 mg, 0.056 mmol) prepared in Example 22 was dissolved in 2 ml of dichcloromethane, followed by the addition of 10 mg (0.058 mmol) of m-chloroperoxybenzoic acid under cooling with ice and stirring. After one hour, a saturated aqueous solution of sodium hydrogencarbonate was added to the reaction mixture and the resulting mixture was extracted with ethyl acetate. The organic phase was washed with water, dried over magnesium sulfate and concentrated. The residue was purified by silica gel thin-layer chromatography to give 14.4 mg of the title compound.

$^1$H-NMR(DMSO-d$_6$) δ(ppm): 2.76(3H, s), 6.78 (1H, dd, J=7.5, 1.1 Hz), 6.96(1H, dt, Jd=0.55 Hz, Jt=7.8 Hz), 7.28 (1H, dd, J=7.6, 0.82 Hz), 7.48(1H, d, J=2.7 Hz), 7.82(2H, d, J=8.6 Hz), 7.89(2H, d, J=8.8 Hz), 10.15(1H, br s), 11.06(1H, br s)

EXAMPLE 25

3-Chloro-N-(3-chloro-1H-pyrrolo[3,2-c]pyridin-7-yl)benzenesulfonamide

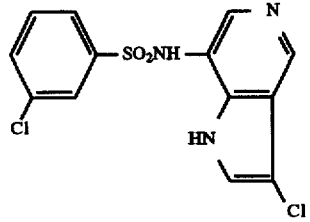

The title compound was prepared in a similar manner to that of Examples 1 and 2.

$^1$H-NMR(DMSO-d$_6$) δ(ppm): 7.41–7.65(2H, m), 7.65–7.77(2H, m), 7.74–7.86(2H, m), 8.40–8.62(1H, br m), 12.38–12.58(1H, br), 13.56–13.74(1H, br)

EXAMPLE 26

4-Acetamido-N-(3-chloro-4-methyl-1H-indol-7-yl)benzenesulfonamide

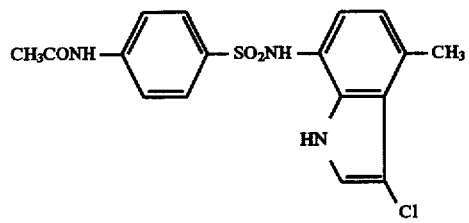

The title compound was prepared in a similar manner to that of Example 1.

M.p.: began to gradually decompose at about 225° C. (recrystallized from ethanol-n-hexane)

¹H-NMR(DMSO-d₆) δ(ppm): 2.03(3H, s), 2.56(3H, 6.54–6.60(2H, m), 7.33(1H, d, J=2.6 Hz), 7.60(2H, d, J=9.0 Hz), 7.64(2H, d, J=9.0 Hz), 9.63(1H, br s), 10.24(1H, br s), 10.92(1H, br s)

EXAMPLE 27

4-Amino-N-(3-chloro-4-methyl-1H-indol-7-yl)benzenesulfonamide

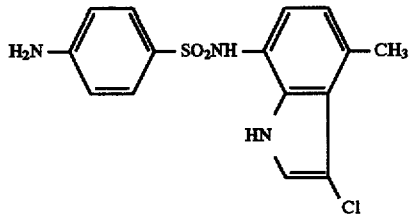

The compound (3.75 g, 9.9 mmol) prepared in Example 26 was dissolved in 25 ml of a 2N aqueous solution of sodium hydroxide. The obtained solution was stirred at 100° C. for 2 hours and brought to room temperature. The pH of the resulting solution was adjusted to 6 with acetic acid to give a precipitate. This precipitate was recovered by filtration and purified by silica gel column chromatography to give 1.1 g of the title compound.

M.p.: began to gradually decompose at about 230° C. (recrystallized from ethanol-n-hexane)

¹H-NMR(DMSO-d₆) δ(ppm): 2.56(3H, s), 5.93(2H, br s), 6.46(2H, d, J=8.8 Hz); 6.59(1H, d, J=7.8 Hz), 6.64(1H, d, J=7.8 Hz), 7.31 (2H, d, J=8.8 Hz), 7.36(1H, d, J=2.9Hz), 9.34(1H, br s), 10.88(1H, br s)

EXAMPLE 28

4-Cyano-N-(3-cyano-1H-indol-7-yl)benzenesulfonamide

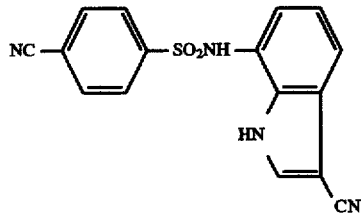

The title compound was prepared in a similar manner to that of Example 1.

M.p.: 250.5° to 252° C. (recrystallized from ethyl acetate-n-hexane)

¹H-NMR(DMSO-d₆) δ(ppm): 6.67(1H, d, J=7.7 Hz), 7.05 (1H, t, J=7.9 Hz), 7.44(1H, d, J=7.7 Hz), 7.78–7.87(2H, m), 7.97–8.05(2H, m), 8.16–8.23(1H, m), 10.28–10.43(1H, br), 11.92–12.09(1H, m)

EXAMPLE 29

4-Carbamoyl-N-(3-chloro-1H-indol-7-yl)benzenesulfonamide

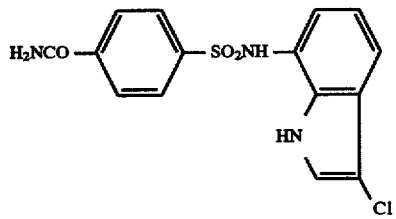

Aqueous hydrogen peroxide (30%, 2.4 ml) and a 6N aqueous solution (360 µl) of sodium hydroxide were added to a solution of 1.0 g (3.01 mmol) of the compound prepared in Example 10 in 4.8 ml of ethanol each in three portions (reaction temperature: about 50° C.). The obtained mixture was further stirred at 50° C. for 30 minutes, acidified with dilute hydrochloric acid and extracted with ethyl acetate. The organic phase was recovered, washed with water, dried over magnesium sulfate, and concentrated. The residue was purified by silica gel column chromatography to give 600 mg of the title compound.

M.p.: began to discolor and decompose at about 248° C. and rapidly decomposed at 252.5° to 253.5° C. (recrystallized from ethanol-n-hexane)

¹H-NMR(DMSO-d₆) δ(ppm): 6.76(1H, d, J=7.5 Hz), 6.95 (1H, dd, J=8.1, 7.5 Hz), 7.27(1H, d, J=8.1 Hz), 7.49(1H, d, J=2.6 Hz), 7.59(1H, br s), 7.76–7.83(2H, m), 7.91–7.98(2H, m), 8.12(1H, br s), 10.10(1H, s), 11.01–11.12(1H, m)

EXAMPLE 30

N-(4-Bromo-1H-indol-7-yl)-4-nitrobenzenesulfonamide

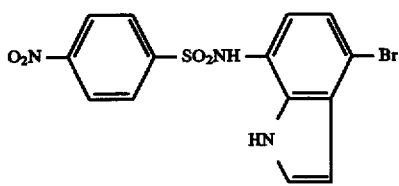

The title compound was prepared in a similar manner to that of Example 1.

¹H-NMR(DMSO-d₆) δ(ppm): 6.35–6.41(1H, m), 6.56 (1H, d, J=8.4 Hz), 7.06(1H, dd, J=8.4, 0.8 Hz), 7.41–7.48 (1H, m), 7.92–8.02(2H, m), 8.30–8.41(2H, m), 10.34(1H, s), 11.18–11.32(1H, m)

EXAMPLE 31

N-(3-Chloro-4-cyano-1H-indol-7-yl)-4-nitrobenzenesulfonamide

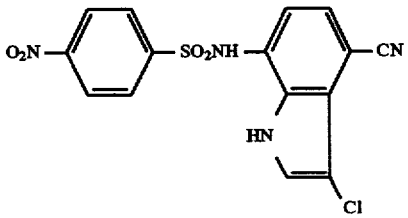

The compound (200 mg, 0.505 mmol) prepared in Example 30 was dissolved in 0.8 ml of N-methylpyrrolidine, followed by the addition of 83 mg (0.91 mmol) of cuprous cyanide. The obtained mixture was stirred at 180° to 190° C. for 3 hours, followed by the addition of 40 ml of ice-water. The resulting mixture was filtered to recover insolubles. The insolubles were washed with water and extracted with hot ethanol and hot chloroform. The organic phase was concentrated and purified by silica gel thin-layer chromatography to give 65 mg of N-(4-cyano-1H-indol-7-yl)-4-nitrobenzenesulfonamide. This product was chlorinated in a similar manner to that of Example 2 to give 42 mg of the title compound.

$^1$H-NMR(DMSO-$d_6$) δ(ppm): 6.98(1H, d, J=8.0 Hz), 7.51 (1H, d, J=8.0 Hz), 7.79(1H, d, J=2.8 Hz), 7.99–8.08(2H, m), 8.31–8.40(2H, m), 10.75–10.95(1H, br), 11.62–11.73(1H, m)

EXAMPLE 32

4-Amino-N-(3-chloro-4-cyano-1H-indol-7-7-yl)-benzenesulfonamide

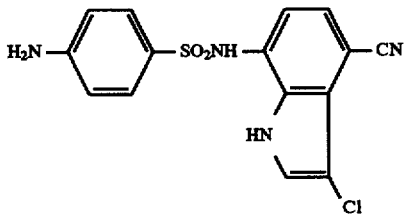

The title compound was prepared from the compound prepared in Example 31 in a similar manner to that of Example 3.

M.p.: began to decompose gradually at about 232° C. and rapidly decomposed at 249.5° to 255° C. (recrystallized from ethanol-n-hexane)

$^1$H-NMR(DMSO-$d_6$) δ(ppm): 6.09(2H, s), 6.52(2H, d, J=8.8 Hz), 7.10(1H, d, J=8.4 Hz), 7.46(2H, d, J=8.8 Hz), 7.50(1H, d, J=8.4 Hz), 7.72–7.79(1H, m), 10.20(1H, s), 11.40–11.59(1H, m)

EXAMPLE 33

6-Amino-N-(3-chloro-1H-indol-7-yl)-3-pyridine-sulfonamide

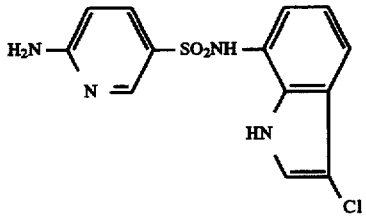

The compound (2.48 g, 7.25 mmol) prepared in Example 14 and lithium iodide (679 mg, 5.07 mmol) were added to 25 ml of ethanol, followed by the addition of 10 ml of liquid ammonia. The obtained mixture was kept at 120° C. by heating in a sealed tube for 26 hours, and thereafter concentrated. The residue was dissolved in ethyl acetate. The obtained solution was washed with a saturated aqueous solution of sodium hydrogencarbonate and water successively, dried over magnesium sulfate and concentrated. The residue was purified by silica gel column chromatography to give 982 mg of the title compound.

M.p.: 206° to 207° C. (recrystallized from ethyl acetate-n-hexane).

$^1$-NMR(DMSO-$d_6$) δ(ppm): 6.37(1H, d, J=8.8 Hz), 6.83–6.94(1H, m), 6.88(2H, br s), 6.99(1H, dd, J=7.9, 7.7 Hz), 7.25(1H, dd, J=7.9, 0.7 Hz), 7.48(1H, d, J=2.7 Hz), 7.56(1H, dd, J=8.8, 2.4 Hz), 8.14(1H, d, J=2.4 Hz), 9.70(1H, s), 10.92–11.03(1H, m)

EXAMPLE 34

N-(3-Chloro-1H-1H-7-yl)-4-(methylsulfinyl-methyl)benzenesulfonamide

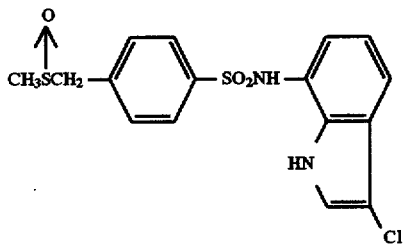

The compound prepared in Example 15 was oxidized in a similar manner to that of Example 24 to give the title compound.

$^1$-NMR(DMSO-$d_6$) δ(ppm): 2.41(3H, s), 3.98(1H, d, J=12.6 Hz), 4.18(1H, d, J=12.8 Hz), 6.77(1H, d, J=7.5 Hz), 6.94(1H, dd, J=7.9, 7.7 Hz), 7.25(1H, d, J=7.9 Hz), 7.43(2H, d, J=8.1 Hz), 7.47(1H, d, J=2.8 Hz), 7.73(2H, d, J=8.1 Hz), 10.01(1H, br s), 11.03(1H, br s)

EXAMPLE 35

N-(3-Chloro-1H-indol-7-yl)-4-(2-sulfamoyl-ethyl)benzenesulfonamide

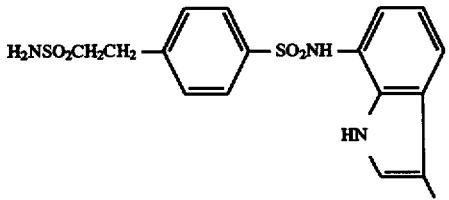

In a similar manner to that of Example 1, 865 mg (3.05 mmol) of the compound prepared in Preparative Example 11 was reacted with 376 mg (2.84 mmol) of the compound prepared in Preparative Example 2 and the reaction mixture was treated. 957 mg of N-(1H-indol-7-yl)-4-(2-sulfamoylethyl)benzenesulfonamide was obtained. This product was chlorinated in a similar manner to that of Example 2 to give 980 mg of the title compound.

M.p.: 217° to 219° C. (dec.) (recrystallized from ethanol-n-hexane)

$^1$-NMR(DMSO-$d_6$) δ(ppm): 3.01-3.06(2H, m), 3.23–3.28 (2H, M), 6.81(1H, dd, J=7.5, 0.37 Hz), 6.88(2H, br s), 6.95(1H, dd, J=8.1, 7.5 Hz), 7.24(1H, dd, J=7.8, 0.37 Hz), 7.42(2H, d, J=8.4 Hz), 7.49(1H, d, J=2.6 Hz), 7.68(2H, d, J=8.2 Hz), 9.99(1H, br s), 11.02(1H, br s)

EXAMPLE 36

N-(3-Chloro-1H-indol-7-yl)-4-[2-(methylsulfonyl)-ethyl]benzenesulfonamide

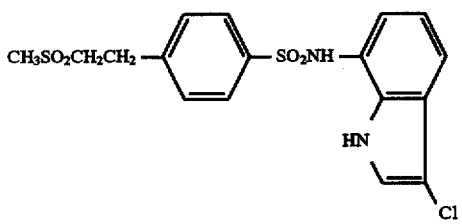

The title compound was prepared in a similar manner to that of Examples 1 and 2.

M.p.: began to discolor at about 180° C. and decomposed at 201° to 203° C. (recrystallized from ethanol-n-hexane)

$^1$H-NMR(DMSO-d$_6$) δ(ppm): 2.92(3H, s), 3.01–3.07(2H, m), 3.40–3.46(2H, m), 6.81(1H, d, J=7.9 Hz), 6.94(1H, dd, J=7.9, 7.7 Hz), 7.24(1H, d, J=7.7 Hz), 7.45(2H, d, J=8.2 Hz), 7.49(1H, d, J=2.7 Hz), 7.68(2H, d, J=8.2 Hz), 9.99(1H, br s), 11.03(1H, brs)

EXAMPLE 37

6-Amino-N-(3-cyano-1H-indol-7-yl)-3-pyridine-sulfonamide

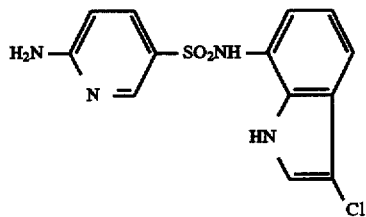

The title compound was prepared by aminating the compound prepared in Example 18 in a similar manner to that of Example 33.

M.p.: 300° C. or above (recrystallized from ethanol-n-hexane)

$^1$H-NMR(DMSO-d$_6$) δ(ppm): 6.39(1H, d, J=9.0 Hz), 6.88 (1H, d, J=7.7 Hz), 6.89(2H, s), 7.11(1H, dd, J=7.9, 7.7 Hz), 7.41(1H, dd, J=7.9, 0.7 Hz), 7.55(1H, dd, J=9.0, 2.6 Hz), 8.12(1H, d, J=2.6 Hz), 8.19(1H, s), 9.72–9.90(1H, br), 11.78–11.92(1H, m)

EXAMPLE 38

4-Acetamide-3-chloro-N-(3-chloro-1H-indol-7-yl)benzenesulfonamide

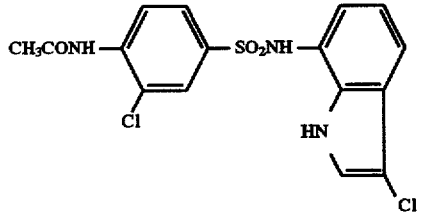

The title compound was prepared in a similar manner to that of Examples 1 and 2.

$^1$H-NMR(DMSO-d$_6$) δ(ppm): 2.14(3H, s), 6.77(1H, d, J=7.7 Hz), 6.98(1H, dd, J=7.9, 7.7 Hz), 7.29(1H, d, J=7.9 Hz), 7.50(1H, d, J=2.7 Hz), 7.64(1H, dd, J=8.6, 2.2 Hz), 7.75(1H, d, J=2.2 Hz), 8.04(1H, d, J=8.6 Hz), 9.69(1H, br s), 10.04(1H, br s), 11.11(1H, br s)

EXAMPLE 39

N-(3-Cyano-1H-indol-7-yl)-8-quinolinesulfonamide

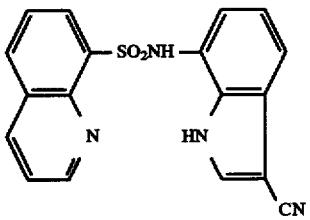

The title compound was prepared in a similar manner to that of Example 1.

$^1$H-NMR(DMSO-d$_6$) δ(ppm): 6.68(1H, d, J=7.3 Hz), 6.89 (1H, dd, J=7.9, 7.7 Hz), 7.25(1H, d, J=8.1 Hz), 7.69–7.74 (2H, m), 8.21(1H, d, J=2.9 Hz), 8.30(1H, dd, J=8.2, 1.3 Hz), 8.35(1H, dd, J=7.4, 1.4 Hz), 8.54(1H, dd, J=8.3, 1.7 Hz), 9.15(1H, dd, J=4.3, 1.7 Hz), 10.04(1H, br s), 12.14(1H, br s)

EXAMPLE 40

5-Chloro-N-(3-cyano-1H-indol-7-yl)-2-thiophenesulfonamide

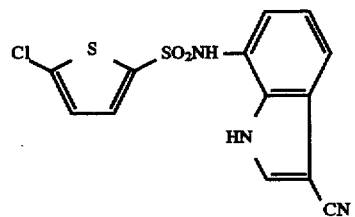

The title compound was prepared in a similar manner to that of Example 1.

$^1$H-NMR(DMSO-d$_6$) δ(ppm): 6.88(1H, ddd, J=7.7, 2.2, 0.73 Hz), 7.16(1H, dd, J=7.9, 7.7 Hz), 7.20(1H, d, J=4.0 Hz), 7.36(1H, d, J=4.2 Hz), 7.51(1H, d, J=8.1 Hz), 8.23(1H, d, J=3.1 Hz), 10.42(1H, br s), 12.01(1H, br s)

EXAMPLE 41

N-(3-Chloro-1H-indol-7-yl)-4-(methoxycarbonyl-amino)benzenesulfonamide

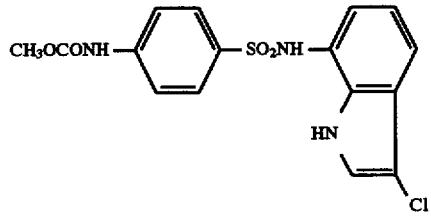

Methyl chloroformate (170 mg, 1.8 mmol) was added to 1 ml of a pyridine solution of 38 mg (0.18 mmol) of the compound prepared in Example 3. The obtained mixture was stirred at room temperature overnight and concentrated. The residue was purified by silica gel column chromatography to give 20 mg of the title compound.

$^1$H-NMR(DMSO-d$_6$) δ(ppm): 3.65(3H, s), 6.80(1H, d, J=7.7 Hz), 6.93(1H, t, J=7.9 Hz), 7.21(1H, dd, J=7.7, 0.37

Hz), 7.45(1H, d, J=2.7 Hz), 7.51(2H, d, J=9.0 Hz), 7.63(2H, d, J=8.8 Hz), 9.85(1H, br s), 10.07(1H, s), 10.97(1H, br s)

EXAMPLE 42

4-Acetyl-N-(3-cyano-1H-indol-7-yl)benzenesulfonamide

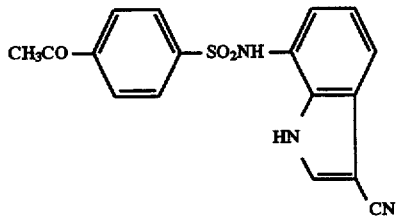

The title compound was prepared in a similar manner to that of Example 1.

$^1$H-NMR(DMSO-$d_6$) δ(ppm): 2.60(3H, s), 6.74(1H, d, J=7.7 Hz), 7.05(1H, dd, J=7.9, 7.7 Hz), 7.42(1H, d, J=7.9 Hz), 7.81–7.88(2H, m), 8.03–8.10(2H, m), 8.21(1H, s), 10.18–10.50(1H, br), 11.92–12.07(1H, m)

EXAMPLE 43

N-(3-Chloro-1H-indol-7-yl)-4-(N-methoxysulfamoyl)benzenesulfonamide

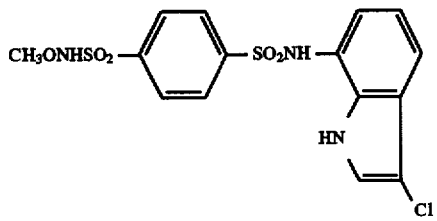

The title compound was prepared in a similar manner to that of Examples 1 and 2.

$^1$H-NMR(DMSO-$d_6$) δ(ppm): 3.65(3H, s), 6.73(1H, d, J=7.6 Hz), 6.96(1H, dd, J=8.0, 7.6 Hz), 7.30(1H, d, J=8.0 Hz), 7.50(1H, d, J=2.4 Hz), 7.98(4H, s), 10.29(1H, br s), 10.76(1H, br s), 11.12(1H, br s)

EXAMPLE 44

N-(3-Cyano-1H-indol-7-yl)-β-styrenesulfonamide

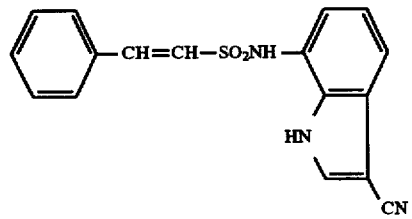

The title compound was prepared in a similar manner to that of Example 1.

$^1$H-NMR(DMSO-$d_6$) δ(ppm): 7.14–7.20(2H, m), 7.32 (2H, s), 7.35–7.47(4H, m), 7.60–7.68(2H, m), 8.23(1H, s), 9.70–10.03(1H, br), 11.85–12.12(1H, br)

EXAMPLE 45

3-Chloro-N-(3-cyano-1H-indol-7-yl)-2-methylbenzenesulfonamide

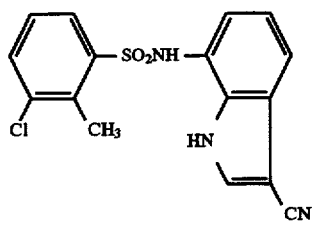

The title compound was prepared in a similar manner to that of Example 1.

$^1$H-NMR(DMSO-$d_6$) δ(ppm): 2.61(3H, S), 6.69(1H, d, J=7.7 Hz), 7.04(1H, t, J=7.9 Hz), 7.36(1H, dd, J=8.1, 7.9 Hz), 7.42(1H, d, J=7.9 Hz), 7.73(1H, dd, J=8.1, 1.1 Hz), 7.77(1H, dd, J=8.0, 0.82 Hz), 8.25(1H, d, J=3.1 Hz), 10.37 (1H, s), 11.99(1H, br s)

EXAMPLE 46

N-(3-Chloro-1H-indol-7-yl)-6-isopropylamino-3-pyridinesulfonamide

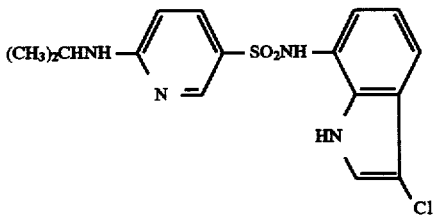

The compound (400 mg, 1.17 mmol) prepared in Example 14 and isopropylamine (0.80 ml, 9.39 mmol) were added to 5 ml of dioxane. The obtained mixture was kept at 100° C. by heating in a sealed tube for 7.5 hours and concentrated. The residue was dissolved in ethyl acetate. The obtained solution was washed with a dilute aqueous solution of citric acid, a saturated aqueous solution of sodium hydrogencarbonate and water successively, dried over magnesium sulfate, and concentrated. The residue was purified by silica gel thin-layer chromatography to give 235 mg of the title compound.

M.p.: began to discolor at about 210° C. and decomposed at 213° to 215° C. (recrystallized from ethyl acetate-n-hexane)

$^1$H-NMR(DMSO-$d_6$) δ(ppm): 1.09(6H, d, J=6.6 Hz), 3.90–4.08(1H, m), 6.39(1H, d, J=9.0 Hz), 6.90–7.05(2H, m), 7.24(1H, d, J=7.9 Hz), 7.33(1H, d, J=7.7 Hz), 7.48(1H, d, J=2.4 Hz), 7.54(1H, dd, J=9.0, 2.6 Hz), 8.22(1H, d, J=2.6 Hz), 9.65–9.84(1H, br), 10.88–11.04(1H, m)

EXAMPLE 47

N-(3-Chloro-1H-indol-7-yl)-6-[[2-(dimethylamino)-ethyl]amino]-3-pyridinesulfonamide

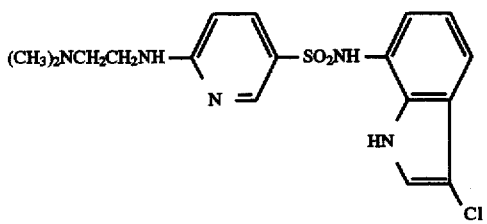

The title compound was prepared from the compound prepared in Example 14 and N,N-dimethylethylenediamine in a similar manner to that of Example 46.

$^1$H-NMR(DMSO-d$_6$) δ(ppm): 2.14(6H, s), 2.35(2H, t, J=6.6 Hz), 3.24–3.44(2H, m), 6.48(1H, d, J=9.0 Hz), 6.92 (1H, d, J=7.7 Hz), 6.99(1H, dd, J=7.9, 7.7 Hz), 7.22(1H, d, J=7.9 Hz), 7.27–7.39(1H, m), 7.47(1H, d, J=2.4 Hz), 7.54 (1H, dd, J=9.0, 2.6 Hz), 8.21(1H, d, J=2.6 Hz), 10.91–11.03 (1H, m)

EXAMPLE 48

N-(3-Cyano-1H-indol-7-yl)-2-furansulfonamide

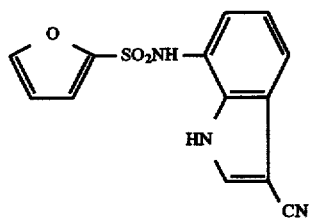

The title compound was prepared in a similar manner to that of Example 1.

$^1$H-NMR(DMSO-d$_6$) δ(ppm): 6.62(1H, ddd, J=3.7, 1.8, 0.37 Hz), 6.78(1H, d, J=7.5 Hz), 7.04(1H, d, J=3.5 Hz), 7.12(1H, t, J=7.9 Hz), 7.49(1H, d, J=8.1 Hz), 7.99–8.00(1H, m), 8.23(1H, d, J=3.1 Hz), 10.49(1H, br s), 12.04(1H, br s)

EXAMPLE 49

N-(3-Chloro-1H-indol-7-yl)-4-[(dimethylamino-sulfonyl)animo]benzenesulfonamide

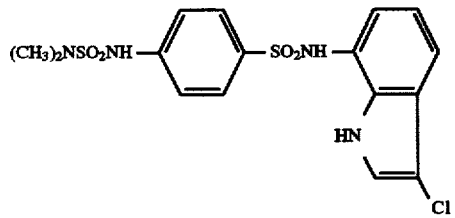

The title compound was prepared from the compound prepared in Example 3 and dimethylsulfamoyl chloride in a similar manner to that of Example 1.

$^1$H-NMR(DMSO-d$_6$) δ(ppm): 2.66(6H, s), 6.81(1H, dd, J=7.7, 0.92 Hz), 6.95(1H, dd, J=7.9, 7.7 Hz), 7.20(2H, d, J=8.8 Hz), 7.23(1H, d, J=8.1 Hz), 7.47(1H, d, J=2.7 Hz), 7.64(2H, d, J=8.8 Hz), 10.98(1H, br s)

EXAMPLE 50

N-(3-Methyl-1H-indol-7-yl)-4-(methylsulfonyl)benzenesulfonamide

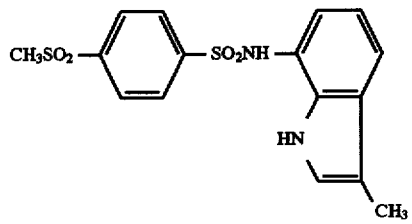

Sodium borohydride (580 mg, 15.3 mmol) and 10% palladium-carbon (150 mg) were added to 25 ml of a suspension of 300 mg (1.58 mmol) of 3-formyl-7-nitro-1H-indole in 2-propanol. The obtained mixture was refluxed for 6 hours, followed by the addition of water. The resulting mixture was filtered to remove the catalyst and the filtrate was extracted with ethyl acetate. The organic phase was washed with a saturated aqueous solution of common salt, dried over magnesium sulfate and distilled in a vacuum to remove the solvent. The residue was dissolved in 5 ml of pyridine and reacted with 170 mg (0.67 mmol) of 4-(methylsulfonyl)benzenesulfonyl chloride in a similar manner to that of Example 1. The obtained reaction mixture was treated in a similar manner to that of Example 1 to give 149 mg of the title compound.

$^1$H-NMR(DMSO-d$_6$) δ(ppm): 2.18(3H, s), 3.24(3H, s), 6.69(1H, d, J=7.7 Hz), 6.81(1H, t, J=7.7 Hz), 7.06(1H, br s), 7.25(1H, d, J=7.8 Hz), 7.95(2H, d, J=8.8 Hz), 8.04(2H, d, J=8.2 Hz), 10.14(1H, br s), 10.40(1H, br s)

EXAMPLE 51

3-Cyano-N-(3-cyano-1H-indol-7-yl)benzenesulfonamide

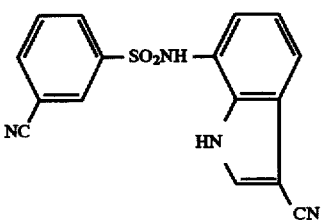

The title compound was prepared in a similar manner to that of Example 1.

$^1$H-NMR(DMSO-d$_6$) δ(ppm): 6.71(1H, d, J=7.2 Hz), 7.09 (1H, dd, J=8.0, 7.6 Hz), 7.49(1H, d, J=8.0 Hz), 7.74(1H, dd, J=8.0, 7.6 Hz), 7.94(1H, d, J=8.0 Hz), 8.11–8.14(2H, m), 8.23(1H, d, J=2.8 Hz), 10.30(1H, br s), 12.05(1H, br s)

EXAMPLE 52

N-(3-Chloro-1H-indol-7-yl)-4-(N-methylmethane-sulfonamido)benzenesulfonamide

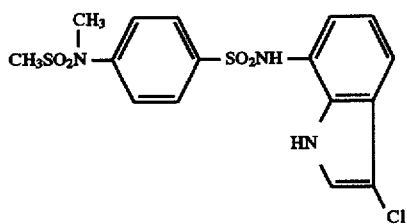

The title compound was prepared in a similar manner to that of Examples 1 and 2.

M.p.: 199° to 201° C. (dec.) (recrystallized from ethanol-n-hexane)

$^1$H-NMR(DMSO-$d_6$) δ(ppm): 2.98(3H, s), 3.24(3H, s), 6.83(1H, dd, J=7.7, 0.37 Hz), 6.96(1H, dd, J=7.9, 7.7 Hz), 7.26(1H, dd, J=7.9, 0.55 Hz), 7.48(1H, d, J=2.7 Hz), 7.50–7.54(2H, m), 7.72–7.76(2H, m), 10.04(1H, br s), 11.02 (1H, br s)

EXAMPLE 53

N-(3-Chloro-1H-indol-7-yl)-4-[(methane-sulfonamido)methyl]benzenesulfonamide

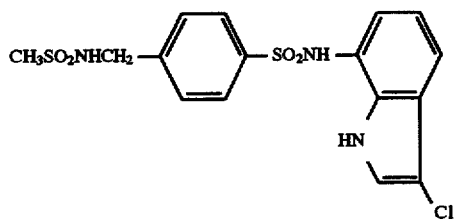

The title compound was prepared in a similar manner to that of Examples 1 and 2.

M.p.: began to discolor at about 180° C. and decomposed at 189° to 191° C. (recrystallized from ethanol-n-hexane)

$^1$H-NMR(DMSO-$d_6$) δ(ppm): 2.81(3H, s), 4.19(2H, d, J=6.0 Hz), 6.79(1H, d, J=7.7 Hz), 6.94(1H, dd, J:7.9, 7.7 Hz), 7.24(1H, d, J=7.9 Hz), 7.47(2H, d, J=8.8 Hz), 7.47–7.49(1H, m), 7.64(1H, t, J=6.4 Hz), 7.72(2H, d, J=8.4 Hz), 10.00(1H, s), 11.03(1H, br s)

EXAMPLE 54

N-(3-Chloro-1H-indol-7-yl)-4-(1-pyrrolidinyl-sulfonyl)benzenesulfonamide

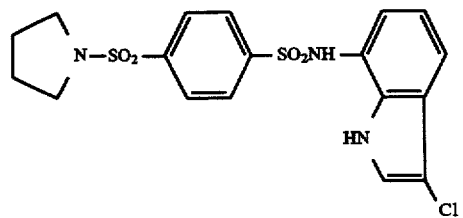

In a similar manner to that of Example 1, the title compound was prepared from 4-(1-pyrrolidinylsulfonyl)benzenesulfonyl chloride and the compound prepared in Preparative Example 10.

$^1$H-NMR(DMSO-$d_6$) δ(ppm): 1.55–1.59(4H, m), 3.07–3.11(4H, m), 6.71(1H, d, J=7.6 Hz), 6.95(1H, ddd, J=8.2, 7.4, 1.2 Hz), 7.30(1H, d, J=8.0 Hz), 7.46(1H, d, J=2.4 Hz), 7.89(2H, d, J=8.8 Hz), 7.92(2H, d, J=8.4 Hz), 10.18 (1H, br s), 11.03(1H, br s)

EXAMPLE 55

N-(3-Cyano-1H-indol-7-yl)-1-methyl-4-imidazolesulfonamide

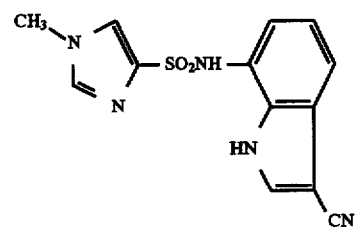

The title compound was prepared in a similar manner to that of Example 1.

$^1$H-NMR(DMSO-$d_6$) δ(ppm): 3.61(3H, s), 7.00(1H, dd, J=7.7, 0.92 Hz), 7.07(1H, dd, J=7.9, 7.7 Hz), 7.35(1H, d, J=7.9 Hz), 7.75–7.76(2H, m), 8.19(1H, d, J=3.1 Hz), 10.03 (1H, br s), 11.92(1H, br s)

EXAMPLE 56

N-(3-Chloro-1H-indol-7-yl)-6-[(2-hydroxyethyl)-amino]-3-pyridinesulfonamide

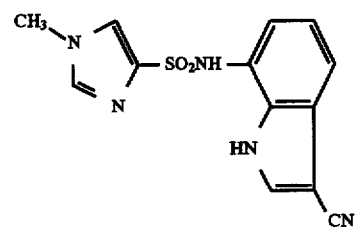

The title compound was prepared from the compound prepared in Example 14 and 2-aminoethanol in a similar manner to that of Example 46.

$^1$H-NMR(DMSO-$d_6$) δ(ppm): 3.24–3.40(2H, m), 3.42–3.52(2H, m), 4.66–4.77(1H, m), 6.48(1H, d, J=9.3 Hz), 6.92(1H, d, J=7.7 Hz), 7.00(1H, t, J=7.7 Hz), 7.24(1H, d, J=7.7 Hz), 7.40–7.62(2H, m), 7.48(1H, d, J=2.2 Hz), 8.22 (1H, d, J=2.6 Hz), 9.63–9.90(1H, br), 10.90–11.07(1H, m)

EXAMPLE 57

N-(3-Chloro-1H-indol-7-yl)-6-mercapto-3-pyridinesulfonamide

The compound (340 mg, 0.99 mmol) prepared in Example 14 and thiourea (151 mg, 1.98 mmol) were added to 5 ml of ethanol. The obtained mixture was heated under reflux for 2 hours and concentrated. Water (1.6 ml) and sodium carbonate (57 mg) were added to the residue. The obtained mixture was stirred at room temperature for 10 minutes, followed by the addition of 85 mg of sodium hydroxide. The obtained mixture was further stirred for 10 minutes and filtered to remove insolubles. The filtrate was acidified with hydrochloric acid to give a precipitate. The precipitate was recovered by filtration, washed with water and dissolved in tetrahydrofuran. The obtained solution was dried over magnesium sulfate and concentrated. The residue was purified by silica gel thin-layer chromatography to give 121 mg of the title compound.

$^1$-NMR(DMSO-d$_6$) δ(ppm): 6.84(1H, d, J=7.6 Hz), 7.03 (1H, t, J=7.6 Hz), 7.28(1H, d, J=9.2 Hz), 7.31(1H, d, J=7.6 Hz), 7.44(1H, dd, J=9.2, 2.4 Hz), 7.48(1H, d, J=2.6 Hz), 7.68(1H, d, J=2.4 Hz), 9.58–9.80(1H, br), 11.08–11.19(1H, m)

EXAMPLE 58

7-(4-Chlorobenzenesulfonamido)-1H-indole-2-carboxylic acid

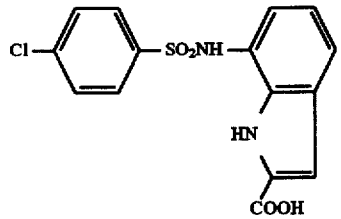

The title compound was prepared in a similar manner to that of Example 1.

$^1$H-NMR(DMSO-d$_6$) δ(ppm): 6.65(1H, d, J=7.6 Hz), 6.87 (1H, dd, J=8.0, 7.6 Hz), 7.00(1H, s), 7.26(1H, d, J=8.0 Hz), 7.56–7.65(2H, m), 7.68–7.77(2H, m), 9.62–10.00(1H, br), 11.40–11.74(1H, br)

EXAMPLE 59

N-(3-Chloro-1H-indol-7-yl)-6-cyclopropylamino-3-pyridinesulfonamide

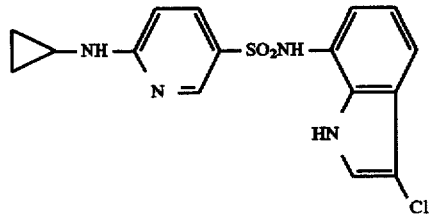

The title compound was prepared in a similar manner to that of Example 46.

M.p.: began to discolor at about 228° C. and decomposed at 233.5° to 235° C. (recrystallized from ethyl acetate-n-hexane)

$^1$H-NMR(DMSO-d$_6$) δ(ppm): 0.36–0.46(2H, m), 0.63–0.75(2H, m), 2.44–2.64(1H, m), 6.45–6.64(1H, m), 6.93(1H, d, J=7.7 Hz), 7.00(1H, dd, J=7.9, 7.7 Hz), 7.24(1H, d, J=7.9 Hz), 7.49(1H, d, J=2.7 Hz), 7.57–7.73(2H, m), 8.25(1H, d, J=2.6 Hz), 9.68–9.90(1H, br), 10.92–11.04(1H, m)

EXAMPLE 60

N-(3-Cyano-1H-indol-7-yl)-5-methyl-3-pyridinesulfonamide

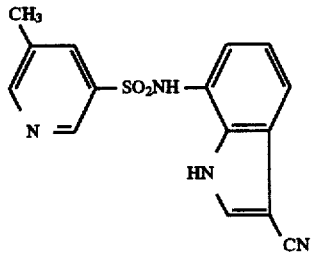

The title compound was prepared in a similar manner to that of Example 1.

M.p.: began to gradually decompose at about 288° C. (recrystallized from ethanol-n-hexane)

$^1$H-NMR(DMSO-d$_6$) δ(ppm): 2.33(3H, s), 6.75(1H, d, J=7.7 Hz), 7.09(1H, dd, J=7.9, 7.7 Hz), 7.48(1H, d, J=7.9 Hz), 7.87–7.91(1H, m), 8.22(1H, d, J=3.1 Hz), 8.58–8.67 (2H, m), 10.28(1H, br s), 11.95–12.08(1H, m)

EXAMPLE 61

N-(3-Chloro-1H-indol-7-yl)-4-(N-methylsulfamoyl)benzenesulfonamide

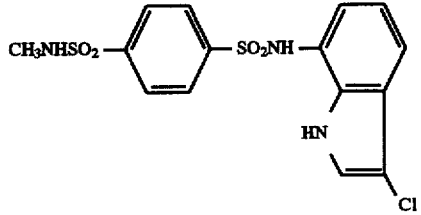

The title compound was prepared in a similar manner to that of Examples 1 and 2.

$^1$H-NMR(DMSO-d$_6$) δ(ppm): 2.39(3H, d, J=5.2 Hz), 6.71 (1H, dd, J=7.8, 2.0 Hz), 6.96(1H, dd, J=8.0, 7.6 Hz), 7.30(1H, d, J=8.0 Hz), 7.48(1H, d, J=2.8 Hz), 7.68(1H, q, J=4.9 Hz), 7.87–7.93(4H, m), 10.20(1H, br s), 11.08(1H, br s)

EXAMPLE 62

N-(3-Chloro-1H-indol-7-yl)-4-[2-(methanesulfonamido)ethyl]benzenesulfonamide

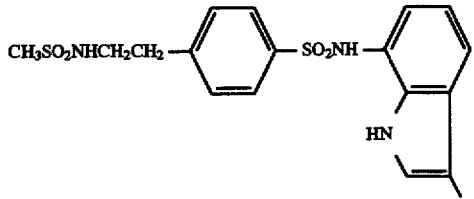

The title compound was prepared in a similar manner to that of Examples 1 and 2.

$^1$H-NMR(DMSO-d$_6$) δ(ppm): 2.73–2.81(5H, m), 3.13–3.19(2H, m), 6.82(1H, d, J=7.7 Hz), 6.95(1H, dd, J=8.1, 7.7 Hz), 7.09(1H, t, J=5.9 Hz), 7.24(1H, d, J=8.1 Hz), 7.39(2H, d, J=8.2 Hz), 7.48(1H, d, J=2.7 Hz), 7.68(2H, d, J=8.4 Hz), 9.97(1H, br s), 11.02(1H, br s)

EXAMPLE 63

N-(3-Chloro-1H-indol-7-yl)-4-(sulfamoylmethyl)benzenesulfonamide

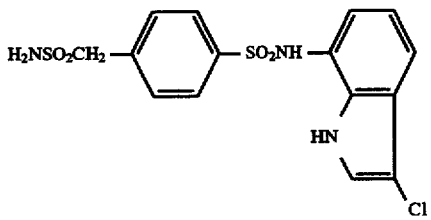

In a similar manner to that of Example 1, 389 mg (1.44 mmol) of the compound prepared in Preparative Example 6 was reacted with 159 mg (1.2 mmol) of the compound prepared in Preparative Example 2 and the reaction mixture was treated. 233 mg of N-(1H-indol-7-yl)-4-(sulfamoylmethyl)benzenesulfonamide was prepared. This product was chlorinated in a similar manner to that of Example 2 to give 160 mg of the title compound.

M.p.: 287 to 288.5 (dec.) (recrystallized from ethanol-n-hexane)

$^1$H-NMR(DMSO-d$_6$) δ(ppm): 4.33(2H, s), 6.84(1H, dd, J=7.7, 0.73 Hz), 6.93(2H, s), 6.92–6.97(1H, m), 7.24(1H, dd, J=7.9, 0.37 Hz), 7.48(1H, d, J=2.7 Hz), 7.48–7.52(2H, m), 7.75–7.79(2H, m), 10.08(1H, br s), 11.04(1H, br s)

EXAMPLE 64

N-(3-Chloro-1H-indol-7-yl)-4-thiocarbamoylbenzenesulfonamide

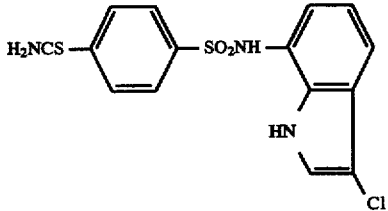

The compound (400 mg, 1.21 mmol) prepared in Example 10 was dissolved in 10 ml of dimethylformamide, followed by the addition of 0.5 ml of triethylamine. Hydrogen sulfide was bubbled through the obtained mixture at a bath temperature of 60° to 70° C. for 45 minutes. The resulting mixture was concentrated and the residue was dissolved in ethyl acetate. The obtained solution was washed with dilute hydrochloric acid, a saturated aqueous solution of sodium hydrogencarbonate and water successively, dried over magnesium sulfate, and distilled in a vacuum to remove the solvent. The residue was purified by silica gel column chromatography to give 355 mg of the title compound.

M.p.: 223° to 225° C. (dec.) (recrystallized from ethanol-n-hexane)

$^1$H-NMR(DMSO-d$_6$) δ(ppm): 6.81(1H, d, J=7.7 Hz), 6.96 (1H, dd, J=7.9, 7.7 Hz), 7.27(1H, d, J=7.9 Hz), 7.50(1H, d, J=2.7 Hz), 7.73–7.80(2H, m), 7.86–7.93(2H, m), 9.58–9.73 (1H, br m), 10.02–10.18(1H, br m), 10.15(1H, s), 11.03–11.12(1H, m)

EXAMPLE 65

5-Bromo-N-(3-cyano-1H-indol-7-yl)-2-pyridinesulfonamide

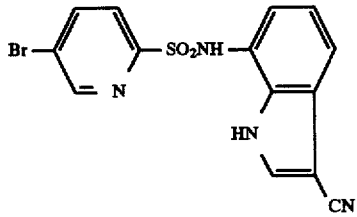

The title compound was prepared in a similar manner to that of Example 1.

M.p.: 245.5° to 246.5° C. (dec.) (recrystallized from ethyl acetate-n-hexane)

$^1$H-NMR(DMSO-d$_6$) δ(ppm): 6.82(1H, d, J=7.7 Hz), 7.07 (1H, dd, J=7.9, 7.7 Hz), 7.44(1H, d, J=7.9 Hz), 7.80(1H, d, J=8.2 Hz), 8.23(1H, d, J=2.2 Hz), 8.29(1H, dd, J=8.2, 2.2 Hz), 8.92(1H, d, J=2.2 Hz), 10.42–10.67(1H, br), 11.93–12.08(1H, m)

EXAMPLE 66

N-(3-Cyano-1H-indol-7-yl)-2-naphthalenesulfonamide

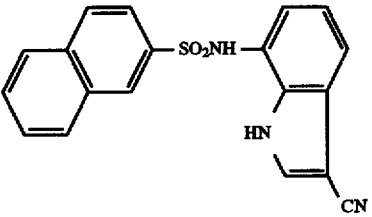

The title compound was prepared in a similar manner to that by Example 1.

$^1$H-NMR(DMSO-d$_6$) δ(ppm): 6.74(1H, dd, J=7.6, 2.8 Hz), 7.00(1H, dd, J=7.9, 7.7 Hz), 7.39(1H, dd, J=8.0, 0.46 Hz), 7.61–7.72(2H, m), 7.80(1H, dd, J=8.6, 1.8 Hz), 8.01 (1H, d, J=8.1 Hz), 8.08(1H, s), 8.10(1H, s), 8.21(1H, d, J=2.9 Hz), 8.34(1H, d, J=1.6 Hz), 10.23(1H, br s), 12.01(1H, br s)

EXAMPLE 67

N-(3-Acetyl-1H-indol-7-yl)-3-chlorobenzenesulfonamide

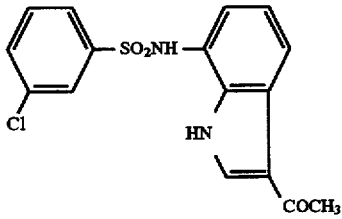

The title compound was prepared in a similar manner to that of Example 1.

$^1$H-NMR(DMSO-d$_6$) δ(ppm): 2.44(3H, s), 6.65(1H, d, J=7.5 Hz), 7.01(1H, dd, J=7.9, 7.7 Hz), 7.53–7.63(2H, m), 7.69–7.73(2H, m), 8.01(1H, dd, J=8.1, 0.73 Hz), 8.26(1H, d, J=2.9 Hz), 10.10(1H, s), 11.75(1H, br s)

EXAMPLE 68

4-Amino-N-(5-bromo-3-cyano-1H-indol-7-yl)-benzenesulfonamide

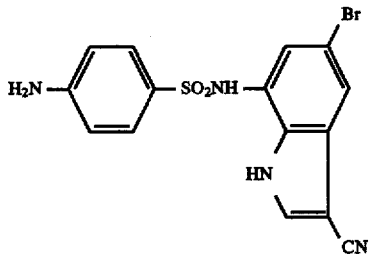

N-(5-Bromo-3-cyano-1H-indol-7-yl)-4-nitrobenzenesulfonamide was prepared from 4-nitrobenzenesulfonyl chloride and the compound prepared in Preparative Example 14 in a similar manner to that of Example 1 and hydrogenated in the presence of platinum oxide at ordinary temperature under normal pressure to give the title compound.

$^1$H-NMR(DMSO-$d_6$) δ(ppm): 6.07(2H, br s), 6.52(2H, d, J=8.4 Hz), 6.97–6.99(1H, m), 7.36(2H, dd, J=8.7, 1.6 Hz), 7.51(1H, br s), 8.25(1H, s), 9.93(1H, d, J=5.5 Hz), 11.97(1H, br s)

EXAMPLE 69

N-(3-Chloro-1H-indol-7-yl)-4-(N-ethylsulfamoyl)-benzenesulfonamide

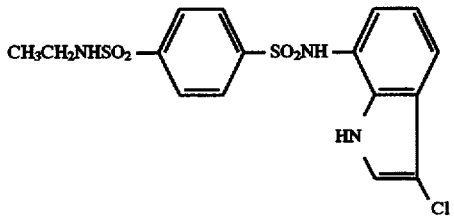

The title compound was prepared in a similar manner to that of Examples 1 and 2.

M.p.: 213° to 215° C. (recrystallized from ethanol-n-hexane)

$^1$H-NMR(DMSO-$d_6$) δ(ppm): 0.90(3H, t, J=7.2 Hz), 2.76 (2H, dq, Jd=5.8 Hz, Jq=7.2 Hz), 6.70(1H, d, J=7.4 Hz), 6.95(1H, dd, J=8.0, 7.6 Hz), 7.29(1H, d, J=8.0 Hz), 7.47(1H, d, J=2.8 Hz), 7.78(1H, t, J=5.6 Hz), 7.90(4H, s), 10.18(1H, br s), 11.06(1H, br s)

EXAMPLE 70

N-(3-Chloro-1H-indol-7-yl)-4-(ethanesulfonamido)-benzenesulfonamide

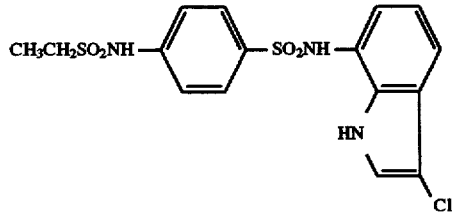

The title compound was prepared in a similar manner to that of Example 4.

M.p.: 214° to 215° C. (dec.) (recrystallized from ethanol-n-hexane)

$^1$H-NMR(DMSO-$d_6$) δ(ppm): 1.14(3H, t, J=7.3 Hz), 3.16 (2H, q, J=7.3 Hz), 6.82(1H, d, J=7.5 Hz), 6.96(1H, dd, J=7.9, 7.7 Hz), 7.23(2H, d, J=8.8 Hz), 7.24(1H, d, J=7.5 Hz), 7.47(1H, d, J=2.6 Hz), 7.66(2H, d, J=8.8 Hz), 9.90(1H, br s), 10.37(1H, br s), 10.96(1H, br s)

EXAMPLE 71

N-(3-Chloro-1H-indol-7-yl)-6-[(2-cyanoethyl)-amino]-3-pyridinesulfonamide

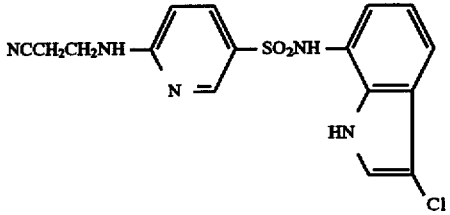

The title compound was prepared in a similar manner to that of Example 46.

$^1$-NMR(DMSO-$d_6$) δ(ppm): 2.72(2H, t, J=6.4 Hz), 3.46–3.55(2H, m), 6.53(1H, d, J=9.0 Hz), 6.90(1H, d, J=7.7 Hz), 6.99(1H, dd, J=7.9, 7.7 Hz), 7.25 (1H, d, J=7.9 Hz), 7.48(1H, d, J=2.6 Hz), 7.61(1H, dd, J=9.0, 2.4 Hz), 7.78–7.87(1H, m), 8.25(1H, d, J=2.4 Hz), 9.70–9.95(1H, br), 10.92–11.04(1H, m)

EXAMPLE 72

N-(3-Chloro-1H-indol-7-yl)-4-(N-methylcarbamoyl)-benzenesulfonamide

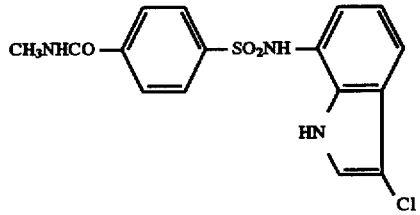

The compound (533 mg, 1.68 mmol) prepared in Example 9 was dissolved in a mixture comprising 5 ml of dimethylformamide and 2.5 ml of dimethyl sulfoxide, followed by the addition of 171 mg (2.53 mmol) of methylamine hydrochloride and 705 μl (5.06 mmol) of triethylamine. 436 μl (2.02 mmol) of diphenylphosphoryl azide was added to the mixture prepared above. The resulting mixture was stirred at room temperature overnight and concentrated. The residue was extracted with ethyl acetate. The ethyl acetate phase was washed with dilute hydrochloric acid, a saturated aqueous solution of sodium hydrogencarbonate and water successively, dried over magnesium sulfate, and concentrated. The residue was purified by silica gel column chromatography to give 465 mg of N-(1H-indol-7-yl)-4-(N-methylcarbamoyl)benzenesulfonamide. This product was chlorinated in a similar manner to that of Example 2 to give 413 mg of the title compound.

M.p.: 252° to 253° C. (dec.) (recrystallized from ethanol-n-hexane).

$^1$H-NMR(DMSO-$d_6$) δ(ppm): 2.76(3H, d, J=4.6 Hz), 6.74 (1H, d, J=7.7 Hz), 6.94(1H, dd, J=7.9, 7.7 Hz), 7.27(1H, d, J=7.9 Hz), 7.49(1H, d, J=2.7 Hz), 7.76–7.83(2H, m), 7.87–7.94(2H, m), 8.61(1H, q, J=4.6 Hz), 10.10(1H, s), 11.03–11.13(1H, m)

EXAMPLE 73

N-(3-Chloro-1H-indol-7-yl)-4-(methylsulfonylmethyl)benzenesulfonamide

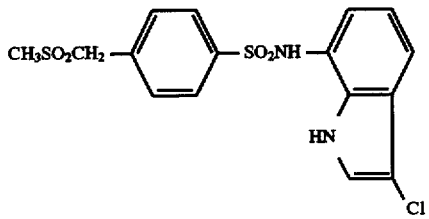

The compound (510 mg) prepared in Example 34 was oxidized with 30% aqueous hydrogen peroxide in a similar manner to that of Example 23 to give 307 mg of the title compound.

M.p.: began to discolor at about 225° C. and gradually decompose at about 235° C. (recrystallized from ethanol-n-hexane)

$^1$H-NMR(DMSO-d$_6$) δ(ppm): 2.88(3H, s), 4.57(2H, s), 6.77(1H, d, J=7.6 Hz), 6.94(1H, dd, J=7.9, 7.7 Hz), 7.25(1H, d, J=8.0 Hz), 7.47(1H, d, J=2.7 Hz), 7.51–7.56(2H, m), 7.73–7.78(2H, m), 10.05(1H, br s), 11.04(1H, br s)

EXAMPLE 74

N-(3-Chloro-1H-indol-7-yl)-4-(N,N-dimethyl-sulfamoyl)benzenesulfonamide

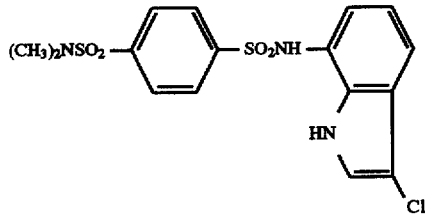

The title compound was prepared in a similar manner to that of Examples 1 and 2.

$^1$H-NMR(DMSO-d$_6$) δ(ppm): 2.57(6H, s), 6.71(1H, dd, J=7.4, 0.6 Hz), 6.97(1H, dd, J=8.0, 7.6 Hz), 7.31(1H, d, J=8.0 Hz), 7.47(1H, d, J=2.8 Hz), 7.86(2H, d, J=8.4 Hz), 7.91(2H, d, J=8.4 Hz), 10.19(1H, br s), 11.04(1H, br s)

EXAMPLE 75

N-(3-Chloro-1H-indol-7-yl)-4-(1-pyrrolidinylcarbonyl)benzenesulfonamide

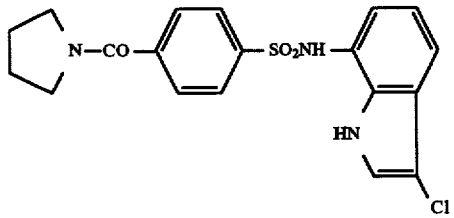

The title compound was prepared in a similar manner to that of Example 1.

$^1$H-NMR(DMSO-d$_6$) δ(ppm): 1.79(2H, dt, Jd=12.8 Hz, Jt=6.4 Hz), 1.85(2H, dt, Jd=13.6 Hz, Jt=6.8 Hz), 3.22(2H, t, J=6.4 Hz), 3.44(2H, t, J=6.8 Hz), 6.78(1H, d, J=7.2 Hz), 6.96(1H, dd, J=8.0, 7.2 Hz), 7.28(1H, d, J=8.0 Hz), 7.47(1H, d, J=2.4 Hz), 7.60(2H, d, J=8.0 Hz), 7.74(2H, d, J=8.4 Hz), 10.06 (1H, br s), 11.01(1H, br s)

EXAMPLE 76

3-Chloro-N-(3-chloro-1H-indol-7-yl)-N-methyl benzenesulfonamide

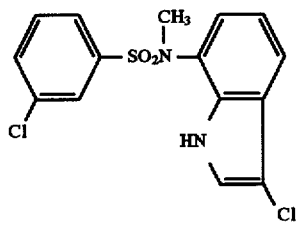

The compound (120 mg, 0.352 mmol) prepared in Example 7 was dissolved in 10 ml of dimethylformamide, followed by the addition of 19.2 mg (0.479 mmol) of sodium hydride (60%). The obtained mixture was stirred at room temperature for 30 minutes, followed by the addition of 30 μl (0.482 mmol) of methyl iodide. After 2 hours, water was added to the resulting mixture and the obtained mixture was extracted with ethyl acetate. The organic phase was washed with water, dried over magnesium sulfate and concentrated. The residue was purified by silica gel thin-layer chromatography to give 87 mg of the title compound.

$^1$H-NMR(DMSO-d$_6$) δ(ppm): 3.26(3H, s), 6.51(1H, dd, J=7.6, 0.64 Hz), 7.00(1H, dd, J=7.9, 7.7 Hz), 7.47(1H, d, J=8.1 Hz), 7.53(1H, d, J=2.7 Hz), 7.54–7.59(2H, m), 7.65 (1H, t, J=7.9 Hz), 7.84(1H, ddd, J=8.1, 2.1, 1.1 Hz), 11.62 (1H, br s)

EXAMPLE 77

N-(3,4-Dichloro-1H-indol-7-yl)-4-(sulfamoylmethyl)benzenesulfonamide

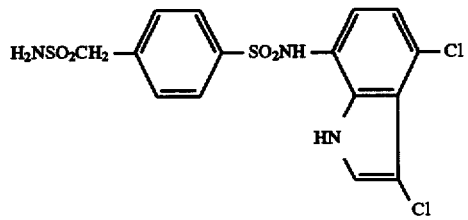

The title compound was prepared in a similar manner to that of Example 1.

M.p.: began to gradually decompose at about 297° C. (recrystallized from ethanol-n-hexane)

$^1$H-NMR(DMSO-d$_6$) δ(ppm): 4.34(2H, s), 6.72(1H, d, J=8.1 Hz), 6.93(2H, s), 6.94(1H, d, J=8.1 Hz), 7.51(2H, d, J=8.1 Hz), 7.57(1H, dd, J=2.7, 0.55 Hz), 7.75(2H, d, J=8.2 Hz), 10.10(1H, br s), 11.44(1H, br s)

EXAMPLE 78

N-(3-Cyano-1H-indol-7-yl)-4-[2-(methylsulfonyl)ethyl]benzenesulfonamide

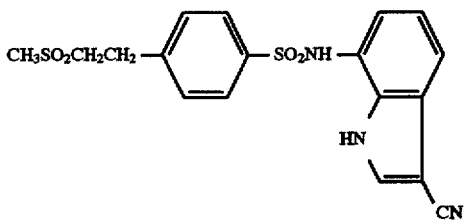

The title compound was prepared in a similar manner to that of Example 1.

$^1$H-NMR(DMSO-d$_6$) δ(ppm): 2.94(3H, s), 3.03–3.08(2H, m), 3.42–3.47(2H, m), 6.77(1H, dd, J=7.7, 0.37 Hz), 7.05 (1H, t, J=7.9 Hz), 7.41(1H, d, J=8.1 Hz), 7.46 (2H, d, J=8.2 Hz), 7.66 (2H, d, J=8.2 Hz), 8.20(1H, s), 10.09(1H, br s), 11.92(1H, br s)

EXAMPLE 79

N-(3-Chloro-1H-indol-7-yl)-4-(N-methylacetamido)-benzenesulfonamide

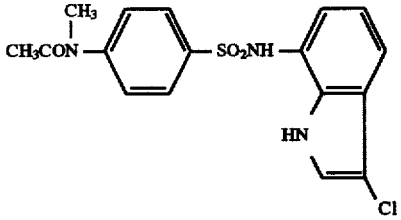

The title compound was prepared in a similar manner to that of Examples 1 and 2.

$^1$H-NMR(DMSO-d$_6$) δ(ppm): 1.84(3H, br s), 3.16(3H, s), 6.81(1H, d, J=7.7 Hz), 6.96(1H, dd, J=8.0, 7.6 Hz), 7.27(1H, d, J=7.9 Hz), 7.45–7.49(2H, m), 7.47(1H, d, J=2.7 Hz), 7.70–7.75(2H, m), 10.02(1H, br s), 11.01(1H, br s)

EXAMPLE 80

N-(3-Chloro-1H-indol-7-yl)-6-hydroxy-3-pyridinesulfonamide

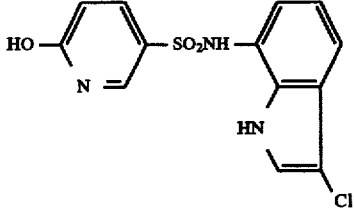

An aqueous solution (1 ml) of 32 mg (0.46 mmol) of sodium nitrite was dropped into a solution prepared by dissolving 100 mg (0.31 mmol) of the compound prepared in Example 33 in 2 ml of glacial acetic acid under cooling with ice. The obtained mixture was stirred for one hour. The pH of the mixture was adjusted to about 8 with an aqueous solution of sodium hydrogencarbonate. The resulting mixture was stirred for 10 minutes and extracted with ethyl acetate. The organic phage was washed with water, dried over magnesium sulfate and concentrated. The residue was purified by silica gel thin-layer chromatography to give 54 mg of the title compound.

M.p.: 244° to 245° C. (dec.) (recrystallized from ethyl acetate-n-hexane)

$^1$H-NMR(DMSO-d$_6$) δ(ppm): 6.39(1H, d, J=9.5 Hz), 6.88 (1H, d, J=7.7 Hz), 7.04(1H, dd, J=7.9, 7.7 Hz), 7.32(1H, d, J=7.9 Hz), 7.50(1H, d, J=2.7 Hz), 7.58(1H, dd, J=9.5, 3.1 Hz), 7.64(1H, d, J=3.1 Hz), 9.76–9.94(1H, br), 11.01–11.13 (1H, m), 11.98–12.15(1H, br)

EXAMPLE 81

N-(3-Chloro-1H-indol-7-yl)-4-[2-(N-methylmethanesulfonamido)ethyl]benzenesulfonamide

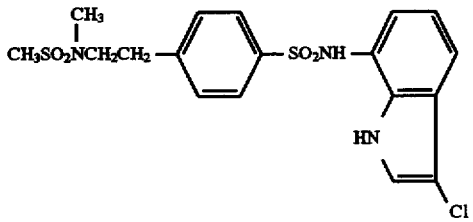

The title compound was prepared in a similar manner to that of Examples 1 and 2.

$^1$H-NMR(DMSO-d$_6$) δ(ppm): 2.69(3H, s), 2.76(3H, s), 2.86(2H, t, J=7.5 Hz), 3.26(2H, t, J=7.5 Hz), 6.78(1H, dd, J=7.4, 0.55 Hz), 6.94(1H, t, J=7.7 Hz), 7.24(1H, dd, J=7.7, 0.37 Hz), 7.39(2H, d, J=8.2 Hz), 7.48(1H, d, J=2.6 Hz), 7.66(2H, d, J=8.2 Hz), 9.94(1H, br s), 11.02(1H, br s)

EXAMPLE 82

N-(3-Chloro-1H-indol-7-yl)-4-(trifluoromethanesulfonamido)benzenesulfonamide

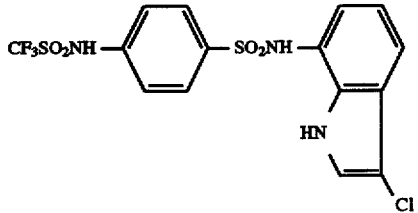

Trifluoromethanesulfonic anhydride (128 μl, 0.76 mmol) was added to a pyridine solution (5 ml) of the compound (62 mg, 0.19 mmol) prepared in Example 3 at 0° C. The obtained mixture was stirred as such overnight and concentrated in a vacuum, followed by the addition of a phosphate buffer of pH7. The resulting mixture was extracted with ethyl acetate. The organic phase was washed with a saturated aqueous solution of common salt, dried over magnesium sulfate and distilled in a vacuum to remove the solvent. The residue was purified by silica gel column chromatography to give 20 mg of the title compound.

$^1$H-NMR(DMSO-d$_6$) δ(ppm): 6.79(1H, d, J=7.7 Hz), 6.94 (1H, dd, J=7.9, 7.7 Hz), 7.16(2H, d, J=8.6 Hz), 7.23(1H, d, J=7.9 Hz), 7.46(1H, d, J=2.7 Hz), 7.58(2H, d, J=8.1 Hz), 9.84(1H, br s), 10.98(1H, br s)

EXAMPLE 83

N-(3-Chloro-1H-indol-7-yl)-4-[(N-methylmethane-sulfonamido)methyl]benzenesulfonamide

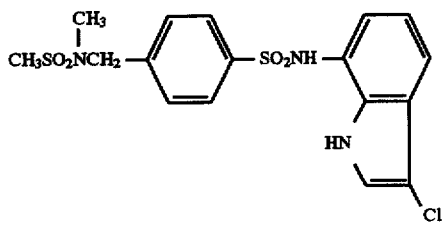

The title compound was prepared in a similar manner to that of Examples 1 and 2.

M.p.: 200.5° to 202° C. (recrystallized from ethanol)

$^1$H-NMR(DMSO-$d_6$) δ(ppm): 2.63(3H, S), 2.94(3H, s), 4.27(2H, s), 6.80(1H, d, J=7.3 Hz), 6.95(1H, dd, J=8.1, 7.5 Hz), 7.25(1H, d, J=7.9 Hz), 7.45(2H, d, J=8.2 Hz), 7.47(1H, d, J=2.7 Hz), 7.74(2H, d, J=8.2 Hz), 10.00(1H, s), 11.00(1H, br s)

EXAMPLE 84

3-Chloro-N-(3-chloro-1H-pyrrolo[2,3-c]pyridin-7-yl)benzenesulfonamide

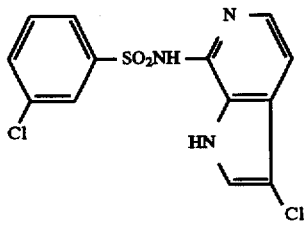

7-Bromo-1H-pyrrolo[2,3-c]pyridine (600 mg, 3.05 mmol) prepared from 2-bromo-3-nitropyridine in a similar manner to that of Preparative Example 1, powdery copper (194 mg) and cuprous chloride (603 mg) were added to 84 ml of a concentrated aqueous solution of ammonia. The obtained mixture was kept at 120° C. by heating in a sealed tube for 15 hours and treated to give 170 mg of 7-amino-1H-pyrrolo[2,3-c]pyridine. This product was reacted and treated in a similar manner to that of Examples 1 and 2 to give 57 mg of the title compound.

$^1$H-NMR(DMSO-$d_6$) δ(ppm): 6.93(1H, d, J=6.6 Hz), 7.45 (1H, dd, J=6.6, 5.8 Hz), 7.53(1H, dd, J=8.0, 7.6 Hz), 7.61(1H, d, J=7.6 Hz), 7.73(1H, d, J=2.8 Hz), 7.85(1H, d, J=8.0 Hz), 7.96(1H, d, J=1.2 Hz), 11.90–12.10(1H, m), 12.72(1H, br s)

We claim:

1. A sulfonamide derivative or a sulfonic ester derivative represented by the general formula (I) or a pharmacologically acceptable salt thereof:

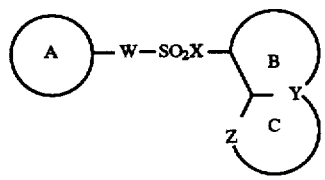

(I)

wherein

A represents a monocyclic or bicyclic aromatic ring which may be substituted,

B represents a six-membered unsaturated hydrocarbon ring or a six-membered unsaturated heterocycle containing one nitrogen atom as the heteroatom, each of which may be substituted, C represents a five-membered heterocycle containing one or two nitrogen atoms which may be substituted with halogen, cyano, lower alkyl, lower alkoxy, hydroxyl, oxo, groups represented by formula —C(O)—r (wherein r represents hydrogen, amino which may be substituted with lower alkyl, lower alkyl, lower alkoxy or hydroxyl), amino substituted with lower alkyl, and trifluoromethyl, W represents a single bond or a group represented by formula —CH=CH—, X represents the formula —N(R$^1$)— or oxygen, Y represents carbon or nitrogen, Z represents a group represented by formula —N(R$^2$)— or nitrogen, and R$^1$ and R$^2$ may be the same or different from each other and each represent hydrogen or lower alkyl; with the provisos that (1) the case wherein A is 4-methylbenzene, W is a single bond, X is a group represented by formula —NH—, B is methoxybenzene and C is unsubstituted imidazole and (2) the case wherein A is 4-(acetamido)benzene or 4-aminobenzene, W is a single bond, X is a group represented by formula —NH—, B is unsubstituted benzene and C is unsubstituted pyrazole, and (3) the case wherein A is a lower alkyl-substituted phenyl, nitro-substituted phenyl or halogen-substituted phenyl, and X is oxygen, are excepted.

2. A compound or pharmacologically acceptable salt thereof as set forth in claim 1, wherein W is a single bond.

3. A compound or pharmacologically acceptable salt thereof as set forth in claim 1, wherein W is a single bond, X and Z are each a group represented by formula —NH—, and Y is carbon.

4. A compound or pharmacologically acceptable salt thereof as set forth in any of claims 1 to 3, wherein B is benzene or pyridine which may be substituted.

5. A compound or pharmacologically acceptable salt thereof as set forth in any of claims 1 to 3, wherein C is pyrrole which may be substituted.

6. A compound or pharmacologically acceptable salt thereof as set forth in claim 1, wherein A is benzene or pyridine which may be substituted, B is benzene which may be substituted, C is pyrrole which may be substituted, W is a single bond, and X and Z are each a group represented by formula —NH—.

7. A compound or pharmacologically acceptable salt thereof as set forth in claim 1, which is selected from the group consisting of 1) 4-amino-N-(3-chloro-1H-indol-7-yl) benzenesulfonamide, 2) N-(3-chloro-1H-indol-7-yl)-4-(methanesulfonamido) benzenesulfonamide, 3) N-(3-chloro-1H-indol-7-yl)-4-cyanobenzenesulfonamide, 4) 6-chloro-N-(3-chloro-1H-indol-7-yl)-3-pyridinesulfonamide, 5) 3-chloro-N-(3-cyano-1H-indol-7-yl) benzenesulfonamide, 6) N-(3-chloro-1H-indol-7-yl)-4-sulfamoylbenzenesulfonamide, 7) N-(3,4-dichloro-1H-indol-7-yl)-4-sulfamoylbenzenesulfonamide, 8) N-(3-chloro-1H-indol-7-yl)-4-(methylsulfonyl)benzenesulfonamide,
9) 4-cyano-N-(3-cyano-1H-indol-7-yl)benzenesulfonamide,
10) 4-carbamoyl-N-(3-chloro-1H-indol-7-yl)benzenesulfonamide,
11) 6-amino-N-(3-chloro-1H-indol-7-yl)-3-pyridinesulfonamide,
12) N-(3-chloro-1H-indol-7-yl)-4-(2-sulfamoylethyl)benzenesulfonamide,
13) N-(3-chloro-1H-indol-7-yl)-4-[2-(methylsulfonyl)ethyl]benzenesulfonamide,
14) 6-amino-N-(3-cyano-1H-indol-7-yl)-3-pyridinesulfonamide,
15) N-(3-chloro-1H-indol-7-yl)-6-isopropylamino-3-pyridinesulfonamide,
16) N-(3-chloro-1H-indol-7-yl)-6-[[2-(dimethylamino)ethyl]amino]-3-pyridinesulfonamide,
17) 3-cyano-N-(3-cyano-1H-indol-7-yl)benzenesulfonamide,
18) N-(3-chloro-1H-indol-7-yl)-4-(N-methylmethanesulfonamido)benzenesulfonamide,
19) N-(3-chloro-1H-indol-7-yl)-4-[(methanesulfonamido)methyl]benzenesulfonamide,
20) N-(3-chloro-1H-indol-7-yl)-6-cyclopropylamino-3-pyridinesulfonamide,
21) N-(3-cyano-1H-indol-7-yl)-5-methyl-3-pyridinesulfonamide,
22) N-(3-chloro-1H-indol-7-yl)-4-(N-methylsulfamoyl)benzenesulfonamide,
23) N-(3-chloro-1H-indol-7-yl)-4-[2-(methanesulfonamido)ethyl]benzenesulfonamide,
24) N-(3-chloro-1H-indol-7-yl)-4-(sulfamoylmethyl)benzenesulfonamide,
25) N-(3-chloro-1H-indol-7-yl)-4-thiocarbamoylbenzenesulfonamide,
26) 5-bromo-N-(3-cyano-1H-indol-7-yl)-2-pyridinesulfonamide,
27) N-(3-chloro-1H-indol-7-yl)-4-(N-ethylsulfamoyl)benzenesulfonamide,
28) N-(3-chloro-1H-indol-7-yl)-4-(ethanesulfonamido)benzenesulfonamide,
29) N-(3-chloro-1H-indol-7-yl)-4-(N-methylcarbamoyl)benzenesulfonamide,
30) N-(3-chloro-1H-indol-7-yl)-4-(methylsulfonylmethyl)benzenesulfonamide,
31) N-(3,4-dichloro-1H-indol-7-yl)-4-(sulfamoylmethyl)benzenesulfonamide,
32) N-(3-chloro-1H-indol-7-yl)-4-(N-methylacetamido)benzenesulfonamide,
33) N-(3-chloro-1H-indol-7-yl)-6-hydroxy-3-pyridinesulfonamide
34) N-(3-chloro-1H-indol-7-yl)-4-[2-(N-methylmethanesulfonamido)ethyl]benzenesulfonamide,
35) 4-carbamoylmethyl-N-(3-chloro-1H-indol-7-yl)benzenesulfonamide,
36) N-(3-chloro-1H-indol-7-yl)-4-[(N-methylmethanesulfonamido)methyl]benzenesulfonamide,
37) N-(3-chloro-1H-indol-7-yl)-4-hydroxybenzenesulfonamide,
38) N-(3-chloro-1H-indol-7-yl)-5-sulfamoyl-2-pyridinesulfonamide,
39) 6-acetamido-N-(3-chloro-1H-indol-7-yl)-3-pyridinesulfonamide,
40) N-(3-chloro-1H-indol-7-yl)-1-methyl-4-imidazolesulfonamide,
41) N-(3-chloro-1H-indol-7-yl)-6-formamido-3-pyridinesulfonamide,
and
42) N-(3-chloro-1H-indol-7-yl)-5-sulfamoylmethyl-2-pyridinesulfonamide.

8. A process which comprises reacting a sulfonic acid represented by the general formula (II):

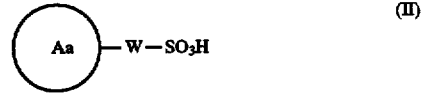

(wherein Aa represents a ring as defined in claim 1 with respect to A which may be protected; and W is as defined in claim 1) or a reactive derivative thereof with a compound represented by the general formula (III):

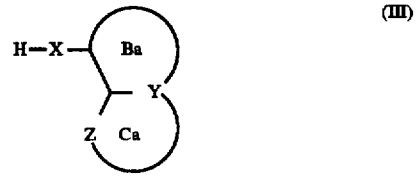

(wherein X, Y and Z are each as defined in claim 1; Ba represents a heterocycle as defined in claim 1 with respect to B which may be protected; and Ca represents a heterocycle as defined in claim 1 with respect to C which may be protected) and, if necessary, deblocking the resulting product when the product has a protective group.

9. A process which comprises reacting a compound represented by the general formula (IV):

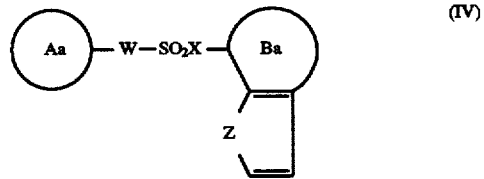

(wherein Aa and Ba and W, X and Z are each as defined in claim 1) with a halogenating agent and, if necessary, deblocking the resulting product when the product has a protective group.

10. A process which comprises reacting a compound represented by the general formula (V):

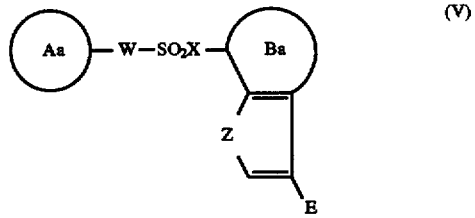

(wherein Aa and Ba, W, X and Z are each as defined in claim 1; and E represents a substituent convertible into a cyano group through dehydration) with a dehydrating agent and, if necessary deblocking the resulting product when the product has a protective group.

11. A process which comprises reacting a compound represented by the general formula (VI):

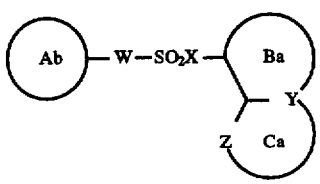 (VI)

(wherein Ab is a ring as defined in claim 1 with respect to A which has a substituent convertible into an amino group through reduction and may be protected; Ba and Ca and W, X, Y and Z are each as defined in claim 1) with a reducing agent and, if necessary, deblocking the resulting product when the product has a protective group.

12. A process which comprises reacting a compound represented by the general formula (VII):

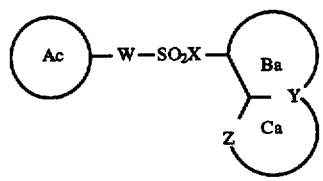 (VII)

(wherein Ac is a ring as defined in claim 1 with respect to A which has a leaving group on the ring or the substituent and may be protected; Ba and Ca and W, X, Y and Z are each as defined in claim 1) with a nucleophile and, if necessary, deblocking the resulting product when the product has a protective group.

13. A drug composition comprising a pharmacologically effective amount of a sulfonamide derivative or a sulfonic ester derivative or a pharmacologically acceptable salt thereof as set forth in claim 1 and a pharmacologically acceptable carrier.

14. The sulfonamide derivative according to claim 1 having the formula

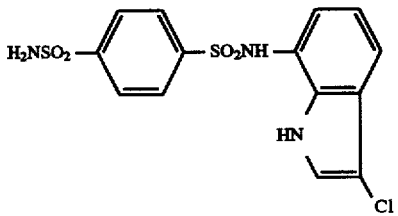

or a pharmacologically acceptable salt thereof.

15. A sulfonamide derivative or a sulfonic ester derivative represented by the general formula (I) or a pharmacologically acceptable salt thereof:

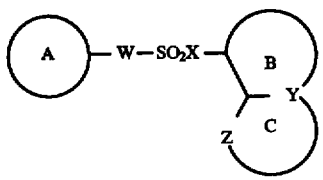 (I)

wherein
A represents a monocyclic or bicyclic aromatic ring which may be substituted, B represents a six-membered unsaturated hydrocarbon ring or a six-membered unsaturated heterocycle containing one nitrogen atom as the heteroatom, each of which may be substituted, C represents a five-membered heterocycle containing one or two nitrogen atoms which may be substituted with halogen, cyano, lower alkyl, lower alkoxy, hydroxyl, oxo, groups represented by formula —C(O)—r (wherein r represents hydrogen, amino which may be substituted with lower alkyl, lower alkyl, lower alkoxy or hydroxyl), amino substituted with lower alkyl, and trifluoromethyl, W represents a single bond or a group represented by formula —CH=CH—, X represents the formula —N($R^1$)—, Y represents carbon or nitrogen, Z represents a group represented by formula —N($R^2$)— or nitrogen, and $R^1$ and $R^2$ may be the same or different from each other and each represent hydrogen or lower alkyl; with the proviso that (1) the case wherein A is 4-methylbenzene, W is a single bond, X is a group represented by formula —NH—, B is methoxybenzene and C is unsubstituted imidazole and (2) the case wherein A is 4-(acetamido)benzene or 4-aminobenzene, W is a single bond, X is a group represented by formula —NH—, B is unsubstituted benzene and C is unsubstituted pyrazole, are excepted.

16. A pharmaceutical composition comprising a pharmacologically effective amount of a sulfonamide derivative or a sulfonic ester derivative, or a pharmacologically acceptable salt thereof as set forth in claim 15; and a pharmacologically acceptable carrier.

17. A method for the treatment of a tumor which comprises administering a pharmacologically effective amount of a sulfonamide derivative or a sulfonic ester derivative, or a pharmacologically acceptable salt thereof as set forth in claim 15, to a patient in need thereof.

18. A method for the treatment of a tumor which comprises administering a pharmacologically effective amount of a sulfonamide derivative or a sulfonic ester derivative, or a pharmacologically acceptable salt thereof as set forth in claim 1, to a patient in need thereof.

19. A sulfonamide derivative or a sulfonic ester derivative represented by formula (I) according to claim 1, wherein Y represents carbon.

* * * * *